US006649359B2

(12) United States Patent
Mutter et al.

(10) Patent No.: US 6,649,359 B2
(45) Date of Patent: Nov. 18, 2003

(54) DIAGNOSIS OF ENDOMETRIAL PRECANCERS

(75) Inventors: George L. Mutter, Chestnut Hill, MA (US); Charis Eng, Columbus, OH (US)

(73) Assignees: The Brigham & Women's Hospital, Inc., Boston, MA (US); The Ohio State University, Columbus, OH (US)

( * ) Notice: Subject to any disclaimer, the term of this patent is extended or adjusted under 35 U.S.C. 154(b) by 0 days.

(21) Appl. No.: 09/871,579

(22) Filed: May 31, 2001

(65) Prior Publication Data

US 2002/0061541 A1 May 23, 2002

Related U.S. Application Data

(60) Provisional application No. 60/208,542, filed on Jun. 1, 2000, and provisional application No. 60/289,449, filed on May 8, 2001.

(51) Int. Cl.$^7$ .............................................. G01N 33/574
(52) U.S. Cl. ....................... 435/7.23; 435/7.1
(58) Field of Search ............................. 435/4, 7.1, 7.2, 435/7.21, 7.23

(56) References Cited

U.S. PATENT DOCUMENTS

| | | |
|---|---|---|
| 4,816,567 A | 3/1989 | Cabilly et al. |
| 5,225,539 A | 7/1993 | Winter |
| 5,585,089 A | 12/1996 | Queen et al. |
| 5,693,762 A | 12/1997 | Queen et al. |
| 5,859,205 A | 1/1999 | Adair et al. |

OTHER PUBLICATIONS

Perren et al Am. J. pathol. vol. 155 p. 1523 (Oct. 1999).*
Ramaswamy et al., *Proc. Natl. Acad. Sci USA* 96: 2110–2115 (1999).
Koshiyama et al., *Cancer J.* 11(6): 277–283 (1998).
Lin et al., *Clinical Cancer Res.* 4(11): 2577–2583 (1998).
Risinger et al., *Clinical Cancer Res.* 4(12): 3005–3010 (1998).
Mutter et al., *J. Natl. Cancer Inst.* 92(11): 924–931 (2000).
Arnold, et al., *Hum. Reprod.*, 16(5):836–845, (2001).
Baak, et al., *J. Pathol.*, 154:335–341, (1988).
Bergeron, et al.,*Am. J. Surg. Pathol.*, 23:1102–1108, (1999).
Bersinger, et al., *Early Pregnancy*, 1:134–140, (1995).
Colgan, et al., *Int. J. Gynecol. Pathol.*, 1:347–352, (1983).
Dahia, et al., *Hum. Mol. Genet.*, 8:185–193, (1999).
Dahia, et al., *Oncogene*, 16:2403–2406, (1998).
Dudley, et al., *Am. J. Obstet. Gynecol.*, 167:1774–1780, (1992).
Dunton, et al., *Am. J. Obstet Gynecol.*, 174:1518–1521, (1996).
Eng, et al., *Int. J. Oncol.*, 12:701–710, (1998).

Eng, et al., *Nat. Biotechnol.*, 15:422–426, (1997).
Fitzgerald, et al., *Oncogene*, 17:727–731, (1998).
Gray, et al., *Obstet. Gynecol.*, 49:385–389, (1977).
Hopfer, et al., *Pathobiology*, 62(2):104–108, (1994).
Jovanovic, et al., *Cancer Res.*, 56:1917–1921, (1996).
Kendall, et al., *Am. J. Surg. Pathol.*, 22:1012–1019, (1998).
Levine, et al., *Cancer Res.*, 58:3254–3258, (1998).
Liaw, et al., *Nature Genet.*, 16:64–67, (1997).
Lin, et al., *Am. J. Pathol.*, 152:1313–1318, (1998).
Marsh, et al., *Genes Chrom. Cancer*, 21:61–69, (1998).
Marsh, et al., *Hum. Mol. Genet.*, 7:507–515, (1998).
Marsh, et al., *J. Med. Genet.*, 35:881–885, (1998).
Maxwell, et al., *Cancer Res.*, 58:2500–2503, (1998).
Mutter, et al., *Am. J. Pathol.*, 146:501–508, (1995).
Mutter, et al., *Cancer Res.*, 55:5080–5084, (1995).
Mutter, et al., *Cancer Res.*, 56:4483–4486, (1996).
Mutter, et al., *Clin. Endrocrinol. Metab.*, 85:2334–2338, (2000).
Mutter, et al., *Int. J. Gynecological Path.*, 19:301–309, (2000).
Mutter, et al., *J. Pathol.*, 190(4):462–469,(2000).
Mutter, et al., *Mol. Pathol.*, 52:257–262 (1999).
Mutter, et al., *Nucleic Acids Res.*, 23:1411–1418, (1995).
Nagase, et al., *Cancer Res.*, 57:1630–1633, (1997).
Novak, et al., eds., Novak's Gynecologic and Obstetric Pathology with Clinical and Endocrine Relations, WB Saunders, Philadelphia, pp. 171–172, (1979).
Parazzini, et al., *Gynecol. Oncol.*, 41:1–16, (1991).
Peiffer, et al., *Cancer Res.*, 55:1922–1926, (1995).
Perren, et al., *Am. J. Pathol.* 155:1253–1260, (1999).
Pinto, et al., *Am. J. Pathol.*, 154:1009–15, (1999).
Podsypanina, et al., *Proc. Natl. Acad. Sci. USA*, 96:1563–8, (1999).
Risinger, et al., *Cancer Res.*, 57:4736–4738, (1997).
Scully, et al., "Uterine corpus. Histological Typing of Female Genital Tract Tumours", New York:Springer–Verlag, pp. 13–31, (1994).
Sherman, et al., *J. Cell Biochem*, 59 Suppl. 23:160–164, (1995).
Silverberg, et al., *Cancer (Phila)*, 49:1504–1510, (1982).
Tashiro, et al., *Cancer Res.*, 57:3935–3940, (1997).
Weiss, et al., *N. Engl. J. Med.*, 302:551–554, (1980).
Winkler, et al., *Obstet. Gynecol.*, 64:185–194, (1984).
Yoshinaga, et al., *Jpn. J. Cancer Res.*, 89(10):985–990, (1998).

* cited by examiner

*Primary Examiner*—Sheela Huff
(74) *Attorney, Agent, or Firm*—Wolf, Greenfield & Sacks, P.C.

(57) ABSTRACT

The invention disclosed herein describes novel methods for diagnosing endometrial precancers by measuring PTEN expression and offers an immunohistochemical biomarker for premalignant disease.

20 Claims, 10 Drawing Sheets

DIAGNOSIS OF ENDOMETRIAL PRECANCERS

RELATED APPLICATIONS

This application claims priority under 35 U.S.C. §119 from U.S. provisional application Ser. No. 60/208,542, filed Jun. 1, 2000, and from U.S. provisional application Ser. No. 60/289,449, filed May 8, 2001.

FIELD OF THE INVENTION

The invention relates to immunological methods for diagnosis of conditions characterized by abnormal levels of PTEN protein.

BACKGROUND OF THE INVENTION

PTEN tumor suppressor gene mutations are the most frequent genetic lesion in the highest incidence female genital tract tumor, endometrioid endometrial adenocarcinoma. The role of PTEN in mediating risk conferred by an abnormal hormonal environment and endometrial hyperplasias is uncertain, because of inadequate reagents for protein expression studies in situ and controversy in precancer diagnosis.

Somatic mutation or deletion of the PTEN tumor suppressor gene has been reported in approximately 40% (1;2) and 40 (3)-76% (4), respectively, of endometrial adenocarcinomas. Further evidence for PTEN function within the female reproductive tract is evident in Pten knockout mice that develop complex proliferative endometrial lesions (5). In humans, familial inheritance of mutant PTEN alleles in Cowden syndrome causes multi-organ development of benign hamartomatous and malignant epithelial tumors (6–8), including an elevated incidence of endometrial adenocarcinoma.

A particular variant of endometrial cancer contributes the bulk of PTEN mutations. These are endometrioid endometrial adenocarcinomas (1;2), the most common type [80% (9;10)] of endometrial cancer in the U.S., readily discriminated by routine histopathology from "non-endometrioid" tumors such as papillary serous and clear cell adenocarcinomas, which also occur at this site. Risk for endometrioid endometrial adenocarcinomas increases in subjects with high estrogen levels unopposed by progestins (11), and appearance of a physically distinctive precancerous lesion (12). Interaction between genetic and hormonal events during the premalignant phases of endometrial tumorigenesis is expected, yet has never been precisely elucidated.

Inaccessibility of premalignant tissues, controversy in their diagnosis, and paucity of high-yield candidate genes are longstanding barriers to productive exploration of endometrial precancer biology. PCR methods have improved the analytical repertoire suited to physically small precancers, including detailed mutational (13), clonal (14), and even lineage reconstruction (15) analysis. However, accurate diagnosis of the precancers themselves, typically termed "hyperplasias" in the widely used World Health Organization nomenclature (16), has been difficult to standardize (17), and even when criteria are agreed upon, reproducibility (18) is suboptimal. Previous reports of PTEN mutation in putative endometrial precancers have used subjective diagnostic criteria (19–21).

Thus, there presently is a need for objective, reproducible, and sensitive methods for diagnosis of endometrial precancers.

SUMMARY OF THE INVENTION

Loss of PTEN function by mutational or other mechanisms is an early and progressive event in endometrial tumorigenesis that may occur in response to known endocrine risk factors, and offers an immunohistochemical biomarker for premalignant disease. Unexpectedly, it has been discovered that individual PTEN-negative glands in endometria (particularly in subjects exposed to unopposed estrogen) are distinguishable by immunohistochemistry using PTEN antibodies or antigen-binding fragments thereof, and that these glands are the earliest recognizable stage of endometrial carcinogenesis, followed by proliferation into dense clusters that form discrete premalignant lesions. Accordingly, the invention provides improved methods and compositions for diagnosing endometrial precancers. The methods of the invention also may be used for identifying individuals at risk for endometrial cancer, or individuals at risk for the recurrence of endometrial cancer after treatment. The methods of the invention may also be used for identifying pharmaceutical candidate compounds active in the onset, progression, or regression of endometrial cancer or precancer.

According to one aspect of the invention, methods for determining the likelihood of a group of endometrial cells or an endometrial gland to become cancerous are provided. The methods include performing PTEN antibody or antigen-binding fragment thereof immunohistochemistry on a group of endometrial cells or one or more endometrial glands and determining the binding of the PTEN antibody or antigen-binding fragment thereof to the group of endometrial cells or glands. A reduced amount of PTEN antibody or antigen-binding fragment thereof bound to the group of endometrial cells or glands relative to a control group of cells indicates that the group of endometrial cells or glands has an increased likelihood of becoming cancerous.

In preferred embodiments, the PTEN antibody or antigen-binding fragment thereof is 6H2.1 antibody or antigen-binding fragment thereof.

In certain embodiments, the group of endometrial cells or the one or more endometrial glands and the control group of cells are present in a tissue sample, such as a tissue biopsy. In other embodiments the control group of cells and the group of endometrial cells or glands are the same cell type. In certain preferred embodiments, the amount of binding of the PTEN antibody or antigen-binding fragment thereof to the group of endometrial cells or glands is 50% or less of the binding of the PTEN antibody or antigen-binding fragment thereof to the control group of cells.

In still other aspects of the invention, the methods also include determining the size of a group of endometrial cells or one or more endometrial glands which have reduced PTEN expression. The size of the cells or glands can be measured in control tissues or in a control biopsy of the same subject to establish a baseline size or average size for the cells or glands. Likewise, PTEN expression can be measured in control tissues or in control biopsies of the same subject. In these embodiments, an increased size of the group of endometrial cells or the glands relative to a control group of cells or glands indicates that the group of endometrial cells or glands has an increased likelihood of becoming cancerous.

In some embodiments of the foregoing methods, the group of endometrial cells or glands are obtained from a subject suspected of having endometrial cancer, or from a subject having or suspected of having elevated unopposed estrogen levels. In still other embodiments, the subject is receiving or has received unopposed estrogen treatment.

According to another aspect of the invention, methods for determining regression, progression or onset of a condition characterized by abnormal levels of PTEN protein are provided. The methods include obtaining a level of the amount of PTEN from a sample obtained from a subject and comparing the level to a control as a determination of regression, progression or onset of the condition. In preferred embodiments of these methods, the PTEN antibody is 6H2.1. In certain embodiments, the subject is undergoing drug therapy for a condition characterized by abnormal levels of PTEN protein.

According to still another aspect of the invention, methods for monitoring the progression of endometrial precancers are provided. The methods include determining the expression of PTEN in endometrial cells or glands by PTEN antibody or antigen-binding fragment thereof immunohistochemistry of an endometrial tissue sample obtained at a first time, determining the expression of PTEN in endometrial cells or glands by PTEN antibody or antigen-binding fragment thereof immunohistochemistry of an endometrial tissue sample obtained at a second time, and comparing the expression of PTEN in the endometrial cells or glands at the first time and the second time. Reduced expression of PTEN at the second time relative to the first time indicates progression of endometrial precancers to a cancerous stage. In preferred embodiments the PTEN antibody is 6H2.1.

In some embodiments, the methods also include determining the size of groups of endometrial cells or glands which have reduced PTEN expression in the endometrial tissue sample obtained at the first time and the endometrial tissue sample obtained at the second time, and comparing the size of the groups of endometrial cells or the glands which have reduced PTEN expression at the first time and the second time. Increased size of the groups of endometrial cells or the glands which have reduced PTEN expression at the second time relative to the first time indicates progression of endometrial precancers to a cancerous stage.

In certain embodiments, the endometrial tissue samples are obtained from a subject suspected of having endometrial cancer or from a subject having or suspected of having elevated unopposed estrogen levels. In other embodiments, the subject is receiving or has received unopposed estrogen treatment or the subject is undergoing drug therapy for endometrial precancer or endometrial cancer.

Similar methods are useful for determining regression of endometrial cancers or precancers, such as following therapeutic invention. Thus, in another aspect of the invention, methods for monitoring the regression of endometrial precancers are provided. The methods include the steps and materials recited above for determination of progression of endometrial precancers. In the analysis of the results, increased expression of PTEN at the second time relative to the first time indicates regression of endometrial precancers from a cancerous stage, and decreased size of the groups of endometrial cells or the glands which have increased PTEN expression at the second time relative to the first time indicates regression of endometrial precancers from a cancerous stage.

In a further aspect of the invention, methods of selecting a treatment for endometrial precancer or endometrial cancer in a subject are provided. The methods include obtaining a level of PTEN expression from an endometrial tissue sample obtained from the subject by immunohistochemical analysis, and selecting the treatment for endometrial precancer or endometrial cancer in the subject based at least in part on the level obtained. These methods also can be used for evaluating a treatment, e.g., to determine its effectiveness.

In certain embodiments, the subject is already receiving drug therapy for endometrial precancer or endometrial cancer. In preferred embodiments, the immunohistochemical analysis is performed using 6H2.1 clone PTEN-reactive monoclonal antibody.

In still another aspect of the invention, kits are provided for identifying endometrial precancer cells in an endometrial tissue sample. The kits include a container containing a PTEN antibody or antigen-binding fragment thereof, a second container containing a detectable compound for detecting the presence of the PTEN antibody or antigen-binding fragment thereof in a sample and instructions for binding the PTEN antibody or antigen-binding fragment thereof to an endometrial tissue sample and for measuring the amount of PTEN antibody or antigen-binding fragment thereof bound to the endometrial tissue sample using the detectable compound. The detectable compounds include, for example, enzyme substrates, detectably labeled second antibodies, etc.

In some embodiments the kits also include a container containing a second detectable compound for histological determination of the size of groups of cells or glands in the endometrial tissue sample.

Other kits for identifying endometrial precancer cells in an endometrial tissue according to the invention include a container containing a PTEN antibody or antigen-binding fragment thereof conjugated to a detectable compound, a second container containing a second detectable compound for histological determination of the size of groups of cells or glands in the endometrial tissue sample and instructions for binding the PTEN antibody or antigen-binding fragment thereof to an endometrial tissue sample and for measuring the amount of PTEN antibody or antigen-binding fragment thereof bound to the endometrial tissue sample using the detectable compound. The detectable compounds include, for example, radiolabels, fluorescent labels, colorimetric compounds.

According to a further aspect of the invention, methods for diagnosing endometrial precancer in a subject are provided. The methods include: obtaining a biological sample of endometrial tissue or cells from a subject, contacting the sample with an endometrial cell marker that specifically binds to endometrial cells, contacting the sample with an antibody or antigen-binding fragment thereof that specifically binds PTEN, determining specific binding between the antibody or antigen-binding fragment thereof and PTEN in the sample, and determining the specific binding between the endometrial cell marker, and agents in the sample. In some embodiments, the determination of specific binding of the antibody or antigen-binding fragment thereof and the specific binding of the endometrial cell marker in the sample, are compared to the specific binding of the antibody or antigen-binding fragment thereof and the specific binding of the endometrial cell marker in a control group of cells as a diagnosis for endometrial precancer in the subject.

In some embodiments, the antibody or antigen-binding fragment thereof is 6H2.1 antibody or an antigen-binding fragment thereof. In some embodiments the endometrial cell marker is selected from the group consisting of: antibodies and antigen-binding fragments thereof, and ligands. In preferred embodiments, the endometrial cell marker comprises an anti-estrogen receptor antibody or an anti-progesterone receptor antibody. More preferably, the anti-estrogen receptor antibody is ER-ID5 and/or the anti-progesterone receptor antibody is IA6. In some embodiments, the endometrial cell marker comprises estrogen or progesterone. In some embodiments, the sample is menstrual fluid.

In some embodiments, the subject is not suspected of having endometrial cancer, and in other embodiments, the subject is not suspected of having endometrial precancer. In some embodiments, the sample is obtained from a subject having or suspecting of having elevated unopposed estrogen levels and in still other embodiments, the sample is obtained from a subject receiving or having received unopposed estrogen treatment.

According to another aspect of the invention, methods for diagnosing endometrial precancer in a subject are provided. The methods include obtaining a biological sample of endometrial tissue or cells from a subject, isolating the endometrial tissue or cells from the sample, contacting the isolated endometrial tissue or cells with an antibody or antigen-binding fragment thereof that specifically binds PTEN, determining specific binding between the antibody or antigen-binding fragment thereof and PTEN in the isolated tissue or cell sample as a diagnosis for endometrial precancer in the subject. Preferred embodiments include comparing the level of specific binding between the antibody or antigen-binding fragment thereof and PTEN in the isolated tissue or cell sample, and the level of specific binding between the antibody or antigen-binding fragment thereof and PTEN in a matched control tissue or cell sample, as a diagnosis for endometrial precancer in the subject.

In preferred embodiments, the antibody or antigen-binding fragment thereof is 6H2.1 antibody or an antigen-binding fragment thereof. In some embodiments, the sample is menstrual fluid. In certain embodiments, the subject is not suspected of having endometrial cancer, and in other embodiments, the subject is not suspected of having endometrial precancer. In some embodiments, the sample is obtained from a subject having or suspecting of having elevated unopposed estrogen levels, and in some embodiments, the sample is obtained from a subject receiving or having received unopposed estrogen treatment.

According to another aspect of the invention kits for diagnosing endometrial precancer in a subject are provided. The kits include antibodies or antigen-binding fragments thereof that specifically bind PTEN, one or more endometrial cell markers, one or more control molecules, and instructions for the use of the antibodies or antigen-binding fragments thereof, cell markers, and control molecules in the diagnosis of endometrial precancer. In some embodiments, the antibodies or antigen-binding fragments thereof are bound to a substrate. In preferred embodiments, the antibody or antigen-binding fragment thereof is 6H2.1 antibody or an antigen-binding fragment thereof. In certain embodiments, the subject is not suspected of having endometrial cancer, and in other embodiments, the subject is not suspected of having endometrial precancer. In some embodiments, the sample is obtained from a subject having or suspecting of having elevated unopposed estrogen levels, and in some embodiments, the sample is obtained from a subject receiving or having received unopposed estrogen treatment.

According to another aspect of the invention, methods for diagnosing endometrial precancer in a subject are provided. The methods include obtaining a biological sample of endometrial tissue or cells from a subject, determining the level of expression of PTEN in the sample, and determining the level of expression of an endometrial cell-associated molecule in the sample. In a preferred embodiment, the method includes comparing the levels of expression of PTEN and one or more endometrial cell-associated molecules to the level of expression of PTEN and one or more endometrial cell-associated molecules in a control sample. In some embodiments, the endometrial cell-associated molecule is selected from the group consisting of: estrogen receptor polypeptides and progesterone receptor polypeptides. In some embodiments, the levels of PTEN and endometrial cell-associated molecule are determined with nucleic acid amplification methods. In some embodiments, the levels of expression of PTEN and the endometrial cell-associated molecules are determined with an immunoassay. In some embodiments, the sample is a body tissue or bodily fluid. In some preferred embodiments, the sample is menstrual fluid. In some preferred embodiments, the sample is endometrial tissue. In certain embodiments, the subject is not suspected of having endometrial cancer, and in other embodiments, the subject is not suspected of having endometrial precancer. In some embodiments, the sample is obtained from a subject having or suspecting of having elevated unopposed estrogen levels, and in some embodiments, the sample is obtained from a subject receiving or having received unopposed estrogen treatment.

According to another aspect of the invention, kits for the diagnosis of endometrial precancer are provided. The kits include oligonucleotides that selectively amplify a nucleic acid sequence that encodes PTEN, oligonucleotides useful for amplifying the nucleic acid sequence that encode one or more endometrial cell-associated molecules, and control nucleic acid primers. In some embodiments the endometrial cell-associated molecule is selected from the group consisting of: estrogen receptor polypeptides or progesterone receptor polypeptides.

According to another aspect of the invention, methods for evaluating the effect of candidate pharmacological compounds on endometrial precancer cell phenotype are provided. The methods include culturing endometrial tissue or cells, contacting the cultured endometrial tissue or cells with an antibody or antigen fragment thereof that specifically binds to PTEN, determining a first amount of specific binding of the antibody or antigen fragment thereof with the endometrial tissue or cells, and contacting the cultured endometrial tissue or cells with a candidate pharmacological agent. The method also includes contacting the cultured endometrial tissue or cells with the antibody or antigen-binding fragment thereof, determining a second amount of specific binding of the antibody or antigen-binding fragment thereof, with the cultured endometrial tissue or cells, and comparing the first and second amounts of specific binding of the antibody or antigen-binding fragment thereof to the tissue or cells. A change in the second amount of specific binding of the antibody or antigen-binding fragment thereof, relative to the first amount of specific binding of the antibody or antigen-binding fragment thereof, indicates the candidate pharmacological compound alters the level of PTEN, wherein a decrease in the relative amount of PTEN indicates the onset of or progression of an endometrial precancer cell phenotype, and where an increase in the relative amount of PTEN indicates the regression of an endometrial precancer cell phenotype. In preferred embodiments, the antibody or antigen-binding fragment thereof is 6H2.1 antibody or an antigen-binding fragment thereof.

In some embodiments, the endometrial tissue or cells are not suspected of having endometrial cancer and in some embodiments, the tissue or cells are not suspected of having endometrial precancer. In some embodiments, the tissue or cells are from a body tissue or bodily fluid, and in some embodiments, the cells are from menstrual fluid. In some embodiments, the tissue or cells are endometrial tissue or cells. In some embodiments, the tissue or cells have not been exposed to unopposed estrogen levels.

According to yet another aspect of the invention methods for evaluating the effect of candidate pharmacological compounds on endometrial precancer cell phenotype are provided. The methods include culturing two matched samples of endometrial tissue or cells, contacting one of the endometrial tissue or cell cultures with a candidate pharmacological agent, contacting each of the endometrial tissue or cell cultures with an antibody or antigen fragment thereof that specifically binds to PTEN, determining the amount of specific binding of the antibody or antigen fragment thereof of each of the endometrial tissue or cell cultures, and comparing the amounts of specific binding of the antibody or antigen-binding fragment thereof to the tissue or cell cultures. A difference in the amount of specific binding of the antibody or antigen-binding fragment thereof in the culture contacted with the candidate pharmacological agent, relative to the amount of specific binding of the antibody or antigen-binding fragment thereof in the culture not contacted with the candidate pharmacological agent, indicates the candidate pharmacological compound alters the level of PTEN. A decrease in the relative amount of PTEN indicates the onset of or progression of an endometrial precancer cell phenotype, and where an increase in the relative amount of PTEN indicates the regression of an endometrial precancer cell phenotype. In preferred embodiments, the antibody or antigen-binding fragment thereof is 6H2.1 antibody or an antigen-binding fragment thereof. In some embodiments, the endometrial tissue or cells are not suspected of having endometrial cancer, and in some embodiments, the tissue or cells are not suspected of having endometrial precancer. In some embodiments, the tissue or cells are from a body tissue or bodily fluid, and in some embodiments the cells are from menstrual fluid. In some embodiments, the tissue or cells are endometrial tissue or cells. In some embodiments, the tissue or cells have not been exposed to unopposed estrogen levels.

The foregoing methods include immunohistochemistry and antibody-based methods but one of ordinary skill in the art would realize that alternative methods for quantifying expression of PTEN would also be useful, including but not limited to: hybridization, selective amplification of nucleic acid molecules encoding PTEN and endometrial cell marker molecules.

The foregoing assay also can be used for assessing exposure to environmental estrogens, such as pesticides.

These and other aspects of the invention will be described in further detail in connection with the detailed description of the invention.

DETAILED DESCRIPTION OF THE INVENTION

Figure 1:
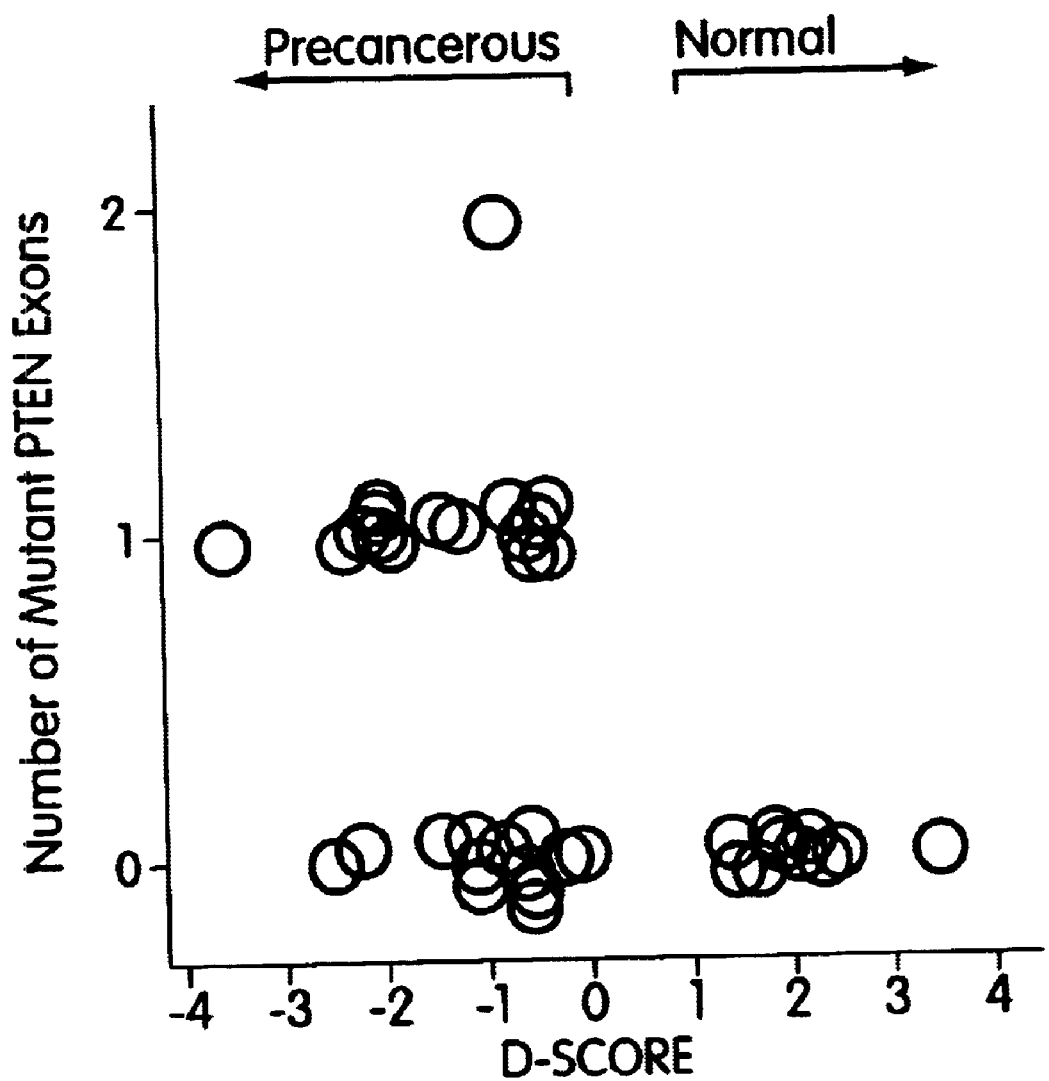
FIG. 1 is a graph of data from thirty nine non-malignant tissues that were classified as precancers or benign based upon computerized morphometric D-Score (12;23). Each tissue is plotted against the number of PTEN mutant exons detected. Benign tissues (D-Score>1, right) did not have PTEN mutations, whereas 55% of morphologic precancers (D-Score<0, left) had mutation in at least one exon. Symbols slightly randomly jittered to improve visibility of overlapping symbols.
Figure 2A:
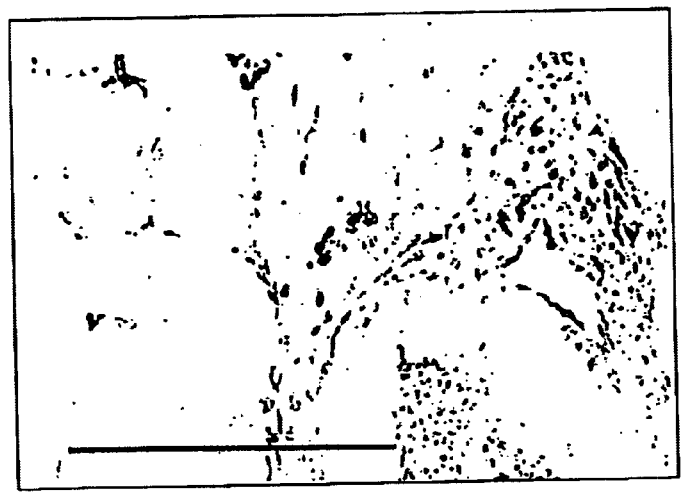
FIG. 2 is a digitized photomicrograph of immunohistochemical detection of PTEN protein (brown precipitate) by antibody 6H2.1 for one patient amongst areas of endometrial adenocarcinoma, endometrial precancer, and benign endometrium. Carcinoma (Panel A) is devoid of PTEN staining, but adjacent endometrial stromal cells and vascular endothelium contain cytoplasmic and nuclear PTEN protein. A geographic zone of precancerous glands is devoid of PTEN protein (Panel B, upper left), contrasting with abundant stromal staining throughout, and an adjacent region of normal endometrial glands (Panel B, right lower) which demonstrate nuclear and cytoplasmic PTEN. High-magnification views in Panels C and E show interface between PTEN negative (precancer) and benign (PTEN positive) glands, including one transition within an individual gland (Panel E). Companion hematoxylin and eosin stained sections, Panels D and F. Scale bar is 100 $\mu$m.
Figure 2B:
Figure 2C:
Figure 2D:
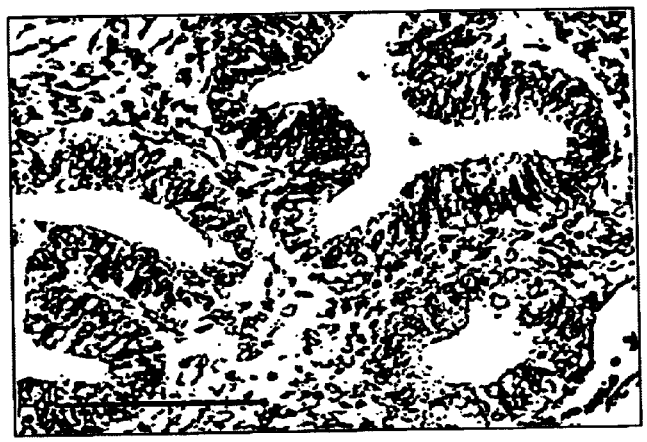
Figure 2E:
Figure 2F:
Figure 3A:
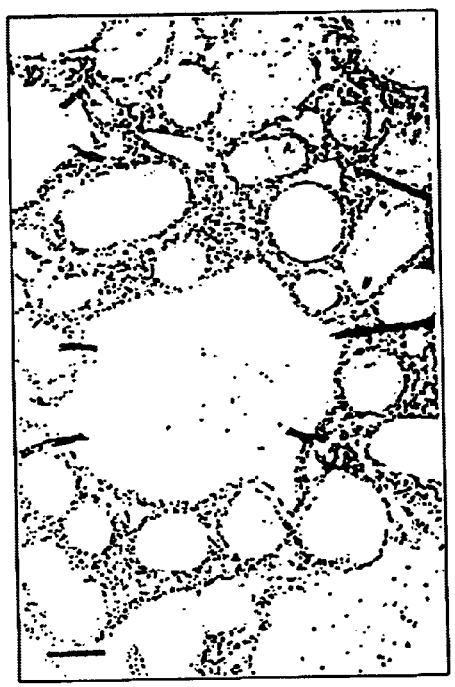
FIG. 3 is a digitized photomicrograph illustrating scattered PTEN-negative glands interposed among PTEN-expressing glands present an interrupted pattern different from the geographic distribution within monoclonal and readily diagnosed precancers shown in FIG. 2. This intermittent pattern was seen at a variety of gland densities ranging from the closely packed architecture characteristic of precancers defined by computerized morphometry (Patient 99-47, Panels A–C) to low densities of a disordered proliferative endometrium (unopposed estrogen effect) (Patient 99-30, Panels D–F). Cytology of PTEN expressing and non-expressing glands may be similar (Panels B–C) or different (Panel E–F). Panels G–H show a persistent estrogen exposed endometrium characterized by cysts, which retains epithelial and stromal PTEN expression. Antibody 6H2.1 immunohistochemistry. Companion hematoxylin and eosin stained sections C,F. Scale bar is 100 $\mu$m.
Figure 3B:
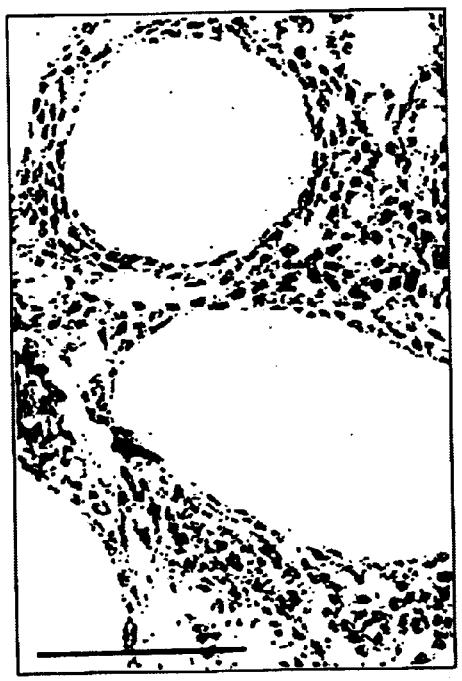
Figure 3C:
Figure 3D:
Figure 3E:
Figure 3F:
Figure 3G:
Figure 3H:

The invention disclosed herein describes novel methods for diagnosing endometrial precancers and offers an immunohistochemical biomarker for premalignant disease.

Unexpectedly, it has been discovered that individual PTEN-negative glands in endometria (particularly those exposed to unopposed estrogen) are distinguishable by immunohistochemistry using PTEN antibodies or antigen-binding fragment thereof, and that these PTEN-negative glands are the earliest recognizable stage of endometrial carcinogenesis, followed by proliferation into dense clusters that form discrete premalignant lesions. Accordingly, the invention provides improved methods and compositions for diagnosing onset, progression, and regression of endometrial precancers.

There are several aspects of the invention that are unexpected. First, it is unexpected that the PTEN marker would be informative at such an early stage of endometrial precancers. For example, in subjects with high estrogen levels unopposed by progesterone, which can happen naturally such as in polycystic ovarian disease (endogenous unopposed estrogen), or pharmacologically such as in estrogen supplementation (exogenous unopposed estrogen), individual endometrial glands have no expression or significantly reduced expression of PTEN, and this identifies them as having altered function, i.e., as premalignant lesions.

Second, it is unexpected that one can track the clinically significant disease over time. Clinically significant disease is determined, in part, by the size of the endometrial gland lesion. Using the methods of the invention, one can establish the average size of the precancerous lesions (which differs from those which are not precancerous) and further, by applying PTEN immunohistochemistry, one can detect those lesions that have reduced PTEN expression. Other detection methods of PTEN expression, such as DNA analysis (e.g., PCR or mutational analysis) do not provide information with respect to the size of the lesion or the PTEN expression in specific glands in the tissue.

Third, one can identify the lesions that are precancerous at a very small size. This type of analysis cannot be done effectively using histology alone. In accordance with the invention, one can observe not only the absolute size of the glands, but also which glands have PTEN expression turned off, and thus have a more robust predictor of endometrial precancer.

Fourth, detection of endometrial precancers as a multifocal or multi-centric disease is also new and unexpected. Cancer typically is thought of as a disease having a single focus; that is, a single cell becomes cancerous, proliferates, and a tumor forms at that locus. The present observations show that endometrial precancers can be formed in several locations simultaneously as several glands can be shown to have reduced PTEN expression and increased size. Without wishing to be bound by any particular theory, it is believed that the initiation event in endometrial precancers, i.e., loss of PTEN expression in a cell, causes the cell to proliferate abnormally. This initiation event unexpectedly has been shown to be a high frequency event in that it occurs in multiple places in the endometrial tissue. To become an endometrial cancer, the lesions must persist and become physically larger. Therefore, an unexpected part of the results is that there is a quantitative threshold event (as opposed to a qualitative threshold event) in that one can observe an abundance of locations having reduced PTEN expression, at least some of which are likely to progress to endometrial cancer.

Fifth, detection of precancers in subject with unopposed estrogen is new and unexpected.

Sixth, detection of precancers in premenopausal women is unexpected and new. The unexpected finding that women with non-disease containing endometrial tissues (e.g. normal endometrial tissues) demonstrate a high level of PTEN null endometrial tissues, thereby providing a tissue model for the onset and development of endometrial precancer and endometrial cancer. Without wishing to be bound by any particular theory, it is believed that the PTEN null tissues may be present and that the progression of such null cells and tissues to cancerous or precancerous is the result of a secondary event, such as exposure to unopposed estrogen or other drug. This surprising finding identifies the premenopausal, non diseased, endometrial tissues as an early carcinogenesis model for endometrial precancer and endometrial cancer. The novel and unexpected carcinogenesis model, utilizing normal (cancer-free) tissue or tissue identified as precancerous or cancerous, may be used to examine the onset, progression or recession of endometrial precancer and endometrial cancer. Such models may also be useful for assessing the effect of candidate pharmacological agents in the onset or treatment of endometrial cancer or precancer.

Seventh, it is new and unexpected that shed cells from the endometrium may be used in the diagnosis of endometrial precancer or endometrial cancer. Such cells may be collected, for example, from menstrual fluid and the expression of PTEN assessed either with immunohistochemical assays or with alternate methods such as selective nucleic acid amplification.

There are several uses for the invention. First, one can use the PTEN immunohistochemistry as an "index diagnostic" to assign risk based on the size of the lesion and the absence of PTEN expression. Therefore, based on these parameters, one can determine whether or not different therapeutic modalities (i.e., chemotherapy, radiation therapy, surgery) should be used. Second, one can use the methods for monitoring progression of endometrial precancers into a cancerous phenotype. By using serial sampling (i.e., biopsy) of the endometrial tissue and observing the size of the lesions and the state of PTEN expression in the lesions (i.e. individual endometrial glands), one can determine whether or not the endometrial precancers are progressing in a way that would indicate whether therapeutic intervention is advised or is successful. Third, one can culture endometrial tissue and test candidate pharmaceutical compounds for effects on PTEN expression.

In the invention, Endometrial Intraepithelial Neoplasia, or "EIN," designates precancers diagnosed using computerized morphometry, and as used herein, "precancers" are synonymous with EIN.

One aspect of the invention is a method to determine the likelihood of a group of endometrial cells or an endometrial gland to become cancerous e.g., for these cells or glands to become precancers or progress to cancerous lesions. The endometrium is the uterine mucous membrane above the level of the internal os. The endometrium consists of a number of subsections such as the endometrial glands, epithelium lining of the endometrial surface, and the stroma (Novak's Gynecologic and Obstetric Pathology with Clinical and Endocrine Relations, E. R. Novak, and J. D. Woodruff, W B Saunders, Philadelphia, 1979. pp171–172). The invention utilizes an agent, such as an antibody, that specifically binds to PTEN protein to assess levels of PTEN in endometrial tissue and cells. PTEN expression in endometrial cells and tissue may also be assessed using nucleic acid analysis, such as selective amplification, or hybridization methods. A level of PTEN below normal or control levels, indicates an increased likelihood that premalignant endometrial disease is present i.e., that the endometrial cells or tissues are precancers.

According to the present invention, an agent that specifically binds to PTEN is used in diagnosis of endometrial precancers. Preferably agents that bind PTEN are PTEN antibodies or antigen-binding fragments thereof, including polyclonal and monoclonal antibodies, prepared according to conventional methodology. Antibodies and antigen-binding fragments thereof that bind PTEN are useful for determining PTEN levels. Thus, terms such as "PTEN antibody bound to the group of endometrial cells or glands" and "binding of the PTEN antibody to the endometrial cell or gland" means the ability of the antibody to bind to and distinguish PTEN from other proteins. As used herein, the term "antibody" is meant to include antibody or antigen-binding fragment thereof.

Antibodies and antigen-binding fragments thereof that bind PTEN molecules and are useful for determining PTEN levels, include but are not limited to: antibodies or antigen-binding fragments thereof that bind specifically to PTEN and antibodies that bind specifically to fragments of PTEN. Certain antibodies useful in the methods of the invention already are known in the art and include anti-PTEN antibodies, including but not limited to: polyclonal rabbit anti-PTEN MMAC1 (Zymed, PCS Biologicals); PTEN clone A2b1 Hu Ms monoclonal (Chemicon); PTEN N-19 and A2B1 (Santa Cruz Biotechnology); PTEN C terminus polyclonal rabbit anti-PTEN (Zymed); PTEN mouse anti-human monoclonal AB-1 (Calbiochem, Clone 6B1); and PTEN mouse anti-human monoclonal AB-2 (Calbiochem, Clone 1A7). Preferably, the anti-PTEN antibody is 6H2.1 (33).

Also useful in the invention are endometrial cell-associated molecules and the nucleic acids that encode them. Examples of endometrial cell-associated molecules are estrogen receptor polypeptides and progesterone receptor polypeptides. Endometrial cell markers are also useful in this invention and these are molecules that bind to the endometrial cell-associated molecules and include, but are not limited to: ligands such as estrogen and progesterone, and antibodies or antigen-binding fragments thereof that specifically bind to estrogen receptor polypeptides or progesterone receptor polypeptides.

Significantly, as is well-known in the art, only a small portion of an antibody molecule, the paratrope, is involved in the binding of the antibody to its epitope (see, in general, Clark, W. R. (1986) *The Experimental Foundations of Modem Immunology*, Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd Fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (Frs), which maintain the tertiary structure of the paratope (see, in general, Clark, W. R. (1986) *The Experimental Foundations of Modem Immunology*, Wiley & Sons, Inc., New York; Roitt, I. (1991) *Essential Immunology*, 7th Ed., Blackwell Scientific Publications, Oxford). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to PTEN molecules. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to PTEN molecules. This process can be repeated through several cycles of reselection of phage that bind to the PTEN molecules. Repeated rounds lead to enrichment of phage bearing particular sequences. DNA sequences analysis can be conducted to identify the sequences of the expressed polypeptides. The minimal linear portion of the sequence that binds to the PTEN molecules can be determined. One can repeat the procedure using a biased library containing inserts containing part of all of the minimal linear portion plus one or more additional degenerate residues upstream or downstream thereof. Yeast two-hybrid screening methods also may be used to identify polypeptides that bind to the PTEN molecules. Thus, PTEN molecules can be used to screen peptide libraries, including phage display libraries, to identify and select peptide binding partners of the PTEN molecules.

As detailed herein, the foregoing antibodies and other binding molecules may be used for example to isolate and identify PTEN protein. The antibodies may be coupled to specific diagnostic labeling agents for imaging of the protein or fragment thereof The antibodies may also be used for immunoprecipitation, immunoblotting PTEN using standard methods known to those of ordinary skill in the art.

The immunohistochemistry assays described herein are carried out on samples (specimens) obtained from subjects. As used herein, a subject is a human, non-human primate, cow, horse, pig, sheep, goat, dog, cat, or rodent. In all embodiments, human subjects are preferred. As used herein, samples may be endometrial tissue or cells and may be obtained through standard methods such as biopsy, curettage or from body fluids such as menstrual fluid.

Particularly, important groups of subjects to which the present invention can be applied are premenopausal subjects, subjects suspected not to have endometrial cancer, subjects suspected of having endometrial cancer, and subjects with elevated unopposed estrogen levels. The term "unopposed estrogen" as used herein, means estrogen without progestin (Harrisons, Vol 14, Principles of Internal Medicine, Eds. Fauci, A. S., E. Braunwald, K. J. Isselbacher, J. D. Wilson, J. B. Martin, D. L. Kasper, S. L. Hauser, D. L. Longo, McGraw-Hill, N.Y., 1999). The term "elevated" as used herein, means levels of unopposed estrogen that exceed normal ranges, which are well known to one of ordinary skill in the medical arts. Elevated estrogen levels may arise from exogenous sources including, but not limited to, administration of estrogen without simultaneous progestin treatment. Elevated unopposed estrogen levels may also arise from endogenous sources such as polycystic ovarian disease.

The assay described herein involves measuring levels of PTEN expression. Levels of PTEN can be determined in a number of ways when carrying out the various methods of the invention. One measurement of the level of PTEN is a measurement of absolute levels of PTEN. This could be expressed, for example, in terms of number of PTEN-positive cells per 100 cells in the tissue sample. Another measurement of the level of PTEN is a measurement of the change in the level of PTEN over time. Still another measurement relates to the number of endometrial glands that express PTEN in a sample. These measurements may be expressed in an absolute amount or may be expressed in terms of a percentage increase or decrease over time. In one particularly important measurement, the level of PTEN is measured in relation to levels in a control cell or gland sample.

Levels of PTEN are advantageously compared to controls according to the invention. The control maybe a predetermined value, which can take a variety of forms. It can be a single cut-off value, such as a median or mean. It can be established based upon comparative groups, such as in groups not having elevated unopposed estrogen levels and groups having elevated unopposed estrogen levels. Another example of comparative groups would be groups having a particular disease, condition or symptoms and groups without the disease, condition or symptoms such as a group with endometrial precancer or endometrial cancer and a group without endometrial precancer or endometrial cancer. Another comparative group would be a group with a family history of a condition such as endometrial cancer and a group without such a family history. The predetermined value can be arranged, for example, where a tested population is divided equally (or unequally) into groups, such as a low-risk group, a medium-risk group and a high-risk group or into quandrants or quintiles, the lowest quandrant or quintile being individuals with the lowest risk or highest amount of PTEN and the highest quandrant or quintile being individuals with the highest risk or lowest amount of PTEN.

Still other controls can be based on other cells or glands within a single endometrial tissue sample. For example, as shown in the Figures, endometrial glands that express PTEN may be located adjacent to endometrial glands that express reduced levels of PTEN. These glands that express PTEN can serve as positive controls for comparison with glands having reduced PTEN antibody staining. Likewise, stromal and other cells in an endometrial tissue sample will express PTEN and can be used as controls.

The predetermined value of a control will depend upon the particular population selected. For example, an apparently healthy population will have a different 'normal' range than will a population which is known to have a condition related to endometrial precancer, endometrial cancer, or elevated unopposed estrogen levels. Accordingly, the predetermined value selected may take into account the category in which an individual falls. Appropriate ranges and categories can be selected with no more than routine experimentation by those of ordinary skill in the art. By "elevated" it is meant high relative to a selected control. Typically the control will be based on apparently healthy normal individuals in an appropriate age bracket.

It will also be understood that the controls according to the invention may be, in addition to predetermined values, samples of materials tested in parallel with the experimental materials. Examples include samples from control populations or control samples generated through manufacture to be tested in parallel with the experimental samples. As used herein a "matched" control means tissue or cells obtained at the same time from the same subject, for example, parts of a single biopsy, or parts of a single cell sample from the subject.

The various assays used to determine the levels of PTEN include: specific binding assays, such as described in the Examples below, using materials which bind specifically to PTEN; gel electrophoresis; and the like. Immunoassays may be used according to the invention including sandwich-type assays, competitive binding assays, one-step direct tests and two-step tests such as described herein. Preferably PTEN levels are determined by nondestructive imaging of PTEN expression. In preferred embodiments, the imaging is real-time imaging and/or permits visualization of PTEN distribution.

In the methods of the present invention, a labeling agent may be directly or indirectly bound to the PTEN-reactive monoclonal antibody in accordance with any known technique. When the labeling agent is directly bound, the labeling agent may desirably have introduced therein a functional group which is capable of binding to a PTEN-reactive monoclonal antibody. When the labeling agent is indirectly bound, bridging molecules such as avidin-biotin, for example, may be present between the labeling agent and the monoclonal antibody.

The labeling agent used in the process of the present invention may typically be an enzyme, a chemiluminescent reagent, a fluorescent reagent, and a radioisotope. Typical enzymes are horseradish peroxidase, alkaline phosphatase, β-galactosidase, luciferase, glucose-6-phosphate dehydrogenase (G6PDH), glucose dehydrogenase (GDH), and the like. Typical chemiluminescent reagents are luminol, isoluminol, an acridinium ester, a dioxethan, and the like. Typical fluorescent reagents are fluorescein isothiocyanate, umbelliferone, chelates of a rare earth metal, and the like. Typical isotopes are $^{125}I$, $^{14}C$ and the like. Other labeling agents will be known to one of ordinary skill in the art.

When the labeling agent employed is an enzyme, a substrate is used for measuring the enzyme activity. The substrate employed is not limited so long as the substrate allows for the enzyme-substrate reaction to be measured as corresponding to the quantity of the enzyme present. For example, when the labeling agent is peroxidase, the substrate employed may be $H_2O_2$ and 3-3'diaminobenzidine (which results in the antibody binding site being stained brown) or $H_2O_2$ and 4-chloro-1-naphthol (resulting in a blue stain), tetramethylbendidine-$H_2O_2$, o-phenylenediamine-$H_2O_2$, 5-aminosalicylic acid-$H_2O_2$, and the like. When the labeling agent is alkaline phosphatase, the substrate employed may be, for example, toluidine salt of 5-bromo-4-chloro-3-indolylphosphate. When the enzyme is β-galactosidase, the substrate employed may be, for example, p-nitrophenyl-β-D-galactopylanoside.

In some embodiments a qualitative determination with the naked eye of the quantity of the labeling agent in the specimen may be preferable. In such cases, a preferred measurement system is a colorimetric system wherein the labeled substance includes an enzyme such as peroxidase, alkaline phosphatase, or β-galactosidase as the labeling agent, and wherein an increase in quantity of the enzyme reaction product may be determined by means of a color development visible to the naked eye.

In addition to the immunohistochemical methods of the invention, selective amplification assays such as PCR, may be used to determine the expression levels of PTEN and endometrial cell-associated molecules.

The specimen used in the process of the invention preferably is endometrial tissue or cells collected from the uterine cavity of a subject. The specimen collected from the uterine cavity may be used as collected. Ordinarily, however, the specimen will be treated with reagents appropriate for preparing the specimen for immunohistochemistry. The specimen may be collected by any usual clinical technique, such as biopsy. Another preferred sample or specimen in the process of the invention is cells or tissue collected from menstrual fluid. The cells may be used as collected or may be isolated from non-endometrial cells using standard cell separation procedures know to those of ordinary skill in the art.

The immunohistochemical assays used in the methods of the invention are standard and well known to one of ordinary skill in the art. Examples of such methods are provided below in the Examples. In general, the assay methods include some or all of the following steps. A specimen is prepared by collecting endometrial cells and/or endometrial tissue from the cavity of the uterus, and optionally treating the cells and/or the tissues in accordance with standard histochemical procedures. For example, the tissue sample may be fixed using formalin or other fixatives and further treated to optimize immunohistochemistry. In preferred embodiments, the tissue specimen is embedded in paraffin according to standard histological methods.

A predetermined amount of the specimen is then immobilized on a carrier, which can be, for example, a plastic or glass microscope slide, etc. The immobilized sample is then contacted with a PTEN-reactive antibody (preferably a monoclonal antibody and particularly preferably antibody clone 6H2.1), which optionally is labeled. The tissue sample can be stained using suitable histological counterstain for visualization of tissue (e.g., hematoxilin/eosin [H&E], methyl green) before or after the sample is contacted with the antibody. If the anti-PTEN antibody is not labeled, it may be labeled subsequent to tissue binding by standard methods, such as by binding a labeled secondary antibody, or by contacting the antibody with a detectable reagent (such as an enzyme substrate, or an avidin-tagged detectable compound).

At various times during the methods, the immobilized sample can be washed to remove excess and/or non-specifically bound antibody, stain, detectable compounds, etc., as necessary. Wash solutions and methods for using them will be known to one of ordinary skill in the art.

The signal intensity of the labeled reagents bound to the tissue specimen is then measured as a determination of the level of PTEN expression. The size of the endometrial glands or of other groups of cells in the tissue specimen can also be measured and the measurement used in the diagnostic methods of the invention as a further predictor of endometrial precancers. The average size of the endometrial glands or of other groups of cells in the tissue specimen may be measured prior to treatment to establish a baseline size.

As disclosed herein, it is also possible to assess likelihood of endometrial precancer by monitoring changes in the absolute or relative amounts of PTEN over time. For example, as disclosed herein, a decrease in PTEN expression in individual endometrial glands correlates with increasing likelihood of endometrial precancer arising in such glands. Accordingly one can monitor PTEN expression over time to determine if the likelihood of endometrial precancer in a subject is changing. Decreases in relative or absolute PTEN of greater than 1.0% may indicate an abnormality, for example an onset or progression of endometrial precancer or endometrial cancer. Preferably, the decrease in PTEN levels, which indicates an abnormality, is greater than 2.0%, 3.0%, 4.0%, 5.0%, 7.0%, 10%, 15%, 20%, 25%, 30%, 40%, 50%, or more. Increases in amounts of PTEN expressed in endometrial glands over time may indicated a decrease in precancer or endometrial cancer remission or regression.

The invention in another aspect provides a diagnostic method to determine the effectiveness of treatments. The "evaluation of treatment" as used herein, means the comparison of a subject's levels of PTEN measured in samples collected from the subject at different sample times, preferably at least 1 month apart following treatment. The preferred time to obtain the second sample from the subject is at least one month after obtaining the first sample, which means the second sample is obtained at any time following the day of the first sample collection, preferably at least 30, 45, 60 or more days after the time of first sample collection.

The comparison of levels of PTEN in two or more samples, taken on different days, allows evaluation of disease progression or regression and of the effectiveness of anticancer treatment. The comparison of a subject's levels of PTEN measured in samples obtained on different days provides a measure to determine the effectiveness of any treatment to avoid or eliminate endometrial precancer.

As will be appreciated by those of ordinary skill in the art, the evaluation of the treatment also may be based upon an evaluation of the symptoms or clinical end-points of the associated disease. Thus, the methods of the invention also provide for determining the regression, progression, or onset of a condition which is characterized by reduced levels of PTEN. In some instances, the subjects to which the methods of the invention are applied are already diagnosed as having a particular condition or disease. In other instances, the measurement will represent the diagnosis of the condition or disease. In some instances, the subjects will already be undergoing therapy for precancer or cancer, while in other instances the subjects will be without present therapy for precancer or cancer.

The diagnostic methods of the invention preferably also include a determination of the size of individual endometrial glands or groups of glands or cells in an endometrial tissue sample. The size of the glands or groups of cells can serve as a further diagnostic marker of endometrial precancers. Typically, progression to a cancerous phenotype includes an increase in cellular proliferation manifested as an increased size of a gland or group of cells. The size of a gland or group of cells can be measured by any convenient method, such as determining the maximum linear dimension of a gland or group of cells. The "maximum linear dimension" of a gland or group of cells is the longest straight linear measurement across the gland or group of cells. Sizes of glands or groups of cells which will confirm or contribute to a diagnosis of endometrial precancer can be absolute sizes or relative sizes as compared to control glands or groups of cells. For absolute sizes, a preferred maximum linear dimension of a gland or group of cells is at least one millimeter. More preferably, the maximum linear dimension is at least 2.0, 2.5, or 3.0 millimeters.

PTEN levels in tissues and cells may also be assessed in tissue and cell culture. Such cultured cells and tissues may be from normal subjects or from subjects believed to have endometrial precancer or endometrial cancer. The cultured cells and tissues may serve as a model for carcinogenesis in endometrial cancer and precancer and may also be used to screen candidate pharmacological agents for effects on the onset, progression or regression of endometrial precancer or endometrial cancer.

Standard methods of cell and tissue culture may be used to culture endometrial cells and tissues. Examples of such methods, although not intended to be limiting, include an explant model of short term culture of intact chunks of endometrial tissues (see: Bersinger N. A., et al., Early Pregnancy 1995; 1: 134–140; Dudley, D. J., et al., Am J. Obstet Gynecol 1992; 167:1774–1780) and the dissociation of stromal and epithelial parts and re-assembly as a co-culture (Arnold, J. T., et al, Hum Reprod 2001; 16(5):836–845; Hopfer, et al., Pathobiology 1994; 62(2):104–108. The invention includes the use of such culture systems for the diagnosis of endometrial precancer and endometrial cancer and for the screening of the effects of candidate pharmacological agents on the onset, progress, and regression of endometrial precancer or endometrial cancer.

The invention also includes kits comprising the PTEN binding agents described herein. The kit includes a package housing a container that contains an agent for determining the level of PTEN in a sample. The kit may also include a control. The kit may also include instructions as described herein. The instructions typically will be in written form and will provide guidance for carrying out the assay embodied by the kit and for making a determination based upon that assay.

An example of a kit may include an antibody or antigen-binding fragment thereof that binds specifically to a PTEN polypeptide, attached to a substrate (e.g. a dipstick). The substrate is then applied to a sample from a patient or to a surface that may contain PTEN and the surface of the substrate is then processed to assess whether specific binding occurs between the antibody and a polypeptide or other component of the sample. As will be understood by one of skill in the art, such binding assay may also be performed with a sample or object contacted with an antibody or antigen-binding fragment thereof and/or PTEN that is in solution, for example in a 96-well plate or applied directly to an object surface.

EXAMPLES

Example 1

Introduction

To determine the earliest stage of endometrial neoplasia in which PTEN mutation occurs, 30 hysterectomy specimens containing endometrioid endometrial adenocarcinomas and coexisting computerized morphometry-diagnosed benign or premalignant endometrial tissue were examined for the presence of mutations.

Methods

Tissue Samples

A series of paraffin embedded endometrial tissues was assembled from the pathology files of Brigham and Women's Hospital, following approval by the Human Studies Committee at that institution. The set, which consisted of tissues from 30 hysterectomies containing endometrioid endometrial adenocarcinoma, and premalignant lesions ("precancers") defined objectively by computerized morphometric analysis (12;23), was used for PTEN mutational analysis. A single region representative of each tissue diagnosis was randomly selected in each hysterectomy. One third of selected hysterectomies also contained histologically "normal" endometrium suitable for analysis, and all contained normal myometrial tissue for use as a DNA control. Endometrial polyps were excluded from analysis.

Histologic Classification Using Computerized Morphometric Analysis

Diagnosis was accomplished using a combination of pathologist review, and objective computerized morphometry. First, carcinomas were distinguished from premalignant lesions by presence of at least one of three diagnostic features: myometrial invasion, solid areas of neoplastic epithelium, or extensively meandering interconnected glandular structures. Endometrial tissues judged not to constitute carcinoma were marked by circumscribing with ink on the glass slide. Computerized morphometric analysis of corresponding delineated regions on H&E stained sections was performed with the QProdit 6.1 system (Leica, Cambridge, UK) as previously (12;23;25)described. For each lesion the D-score was calculated, incorporating volume percentage stroma (VPS), standard deviation of shortest nuclear axis (SDSNA), and gland outer surface density (OUTSD), and then classed as precancers (D<0), indeterminate (0<D<1), or benign (D>1) based on the previously developed outcome-predictive formula D=0.6229+(0.0439×VPS)−(3.9934×Ln (SDSNA))−(0.1592×OUTSD) (12;23). Endometrial areas scored as benign were subclassified by pathologist review. Atrophic, cycling, or reactive endometrium was identified and grouped as "normal." Unopposed estrogen exposed endometria were diagnosed by appearance of occasional glandular cysts in a disordered proliferative field, without sufficient glandular crowding or atypia to qualify as a precancer. The source of unopposed estrogen was either endogenous (anovulatory cycles) or exogenous (pharmacological estrogens). Subjective criteria for EIN diagnosis include three steps: 1) exclusion of overlapping benign changes such as polyps, reactive change, and confounding effects of progestin administration; 2) gland crowding, estimated by reductions in volume percentage stroma to less than half the sample volume; and 3) altered cytology.

DNA Isolation and PTEN Mutational Analysis

Details of microsatellite instability testing (15), and clonal analysis (14;26–28) (24) of 30 hysterectomies used for PTEN DNA mutational analysis have been previously reported. DNA from desired areas of paraffin sections was isolated by selective ultraviolet irradiation (14), typically encompassing a 3 mm diameter region of tissue containing dozens of individual glands. PTEN coding sequence was amplified with intron-based PCR primers thereby avoiding co-amplification of the intronless PTEN pseudogene on chromosome 9 (29). A GC-clamp at the 5' end of one PCR primer stabilized the termini of double-stranded PCR products, increasing sensitivity of mutation detection by altered migration in a chemical denaturing gradient (Denaturing Gradient Gel Electrophoresis, or "DGGE"). DGGE was performed using published methods (30). The oligonucleotide primers used are listed beginning from the 5' end:

```
primer 1FGC, CGT CTG CCA TCT CTC TCC TCC T;                          (SEQ ID NO: 1)

primer 1RGC, CGC CCG CCG CGC CCC GCG CCC GGC CCG CCG CCC CCG          (SEQ ID NO: 2)
CCC GAA ATA ATA AAT CCG TCT ACT CCC ACG TTC T;

primer 2FGC, CGT CCC GCG TTT GAT TGC TGC ATA TTT CAG;                 (SEQ ID NO: 3)

primer 2RGC, CGC CCG CCG CGC CCC GCG CCC GTC CCG CCG CCC CCG          (SEQ ID NO: 4)
CCC GTC TAA ATG AAA ACA CAA CAT G;

primer 3FGC, CGC CCG CCG CGC CCC GCG CCC GGC CCG CCG CCC CCG          (SEQ ID NO: 5)
CCC GTA AAT GGT ATT TGA GAT TAG;

primer 3RGC, GCG CGA AGA TAT TTG CAA GCA TAC A;                       (SEQ ID NO: 6)

primer 4FGC, CGC CCG CCG CGC CCC GCG CCC GTC CCG CCG CCC CCG          (SEQ ID NO: 7)
CCC GAA ATA ATA AAC ATT ATA AAG ATT CAG GCA ATG;

primer 4RGC, GAC AGT AAG ATA CAG TCT ATC;                             (SEQ ID NO: 8)

primer 5.1FGC, CGC CCG CCG CGC CCC GCG CCC GTC CCG CCG CCC            (SEQ ID NO: 9)
CCG CCC GTT TTT TCT TAT TCT GAG GTT ATC;

primer 5.1RGC, TCA TTA CAC CAG TTC GTC C;                             (SEQ ID NO: 10)

primer 5.2FGC, TCA TGT TGC AGC AAT TCA C;                             (SEQ ID NO: 11)

primer 5.2RGC, CGC CCG CCG CGC CCC GCG CCC GTC CCG CCG CCC            (SEQ ID NO: 12)
CCG CCC GGAA GAG GAA AGG AAA AAC ATC;

primer 6FGC, GCG CGT TTC AAT TTG GCT TCT CTT T;                       (SEQ ID NO: 13)

primer 6RGC, CGC CCG CCG CGC CCC GCG CCC GGC CCG CCG CCC CCG          (SEQ ID NO: 14)
CCC GAA ATA ATA AAT AAG AAA ACT GTT CCA ATA C;

primer 7FGC, CGT CCC GCA ATA CTG GTA TGT ATT TAA C;                   (SEQ ID NO: 15)

primer 7RGC, CGC CCG CCG CGC CCC GCG CCC GGC CCG CCG                  (SEQ ID NO: 16)
CCC CCG CCC GGA TAT TTC TCC CAA TGA AAG;

primer 8FGC, CGG TTT CAC TTT TGG GTA AAT A;                           (SEQ ID NO 17)

primer 8RGC, CGC CCG CCG CGC CCC GCG CCC GTC CCG CCG CCC CCG          (SEQ ID NO: 18)
CCC GAC CCC CAC AAA ATG TTT AAT;

primer 9FGC, CGC CCG CCG CGC CCC GCG CCC GGC CCG CCG CCC CCG          (SEQ ID NO: 19)
CCC GTC ACT AAA TAG TTT AAG ATG;

primer 9RGC, TTC ATT CTC TGG ATC AGA GT.                              (SEQ ID NO: 20)
```

PCR products were electrophoresed 16 hr at 100 volts at 60° C. on a 10% polyacrylamide gel containing 5% glycerol and a linear 15%–50% urea-formamide gradient. Samples were visualized by ultraviolet transillumination of the ethidium bromide stained gel, and usually appeared as "doublets" of mutant PTEN products offset by wild-type DNA contributed by contaminating normal tissues or the companion allele. Aberrant bands were reamplified and a nested sequencing primer employed for generation of fluorescent labeled terminated sequencing products that were analyzed on an automated DNA sequencer as previously described (6). DGGE gels and sequencing chromatograms were independently read by three sets of individuals.

Statistical Analysis

Fishers exact tests were performed on the data in Table I using SYSTAT v.9.0 (SPSS Inc., Chicago, Ill.).

Results

Somatic (occurring in tumor only) PTEN mutations were found in 25 of 30 (85%) endometrial carcinomas and 16 of 29 (55%) precancers (Table I). Two-tail Fishers exact test of diagnosis (cancer/EIN) by PTEN mutation (present/absent) showed that cancers had a significantly (p=0.025) increased PTEN mutation rate compared to their precursors. No normal endometria showed mutations in PTEN (Table I). Interestingly, among both cancers and precancers the majority (73% and 52%, respectively) harbored a single mutation, but two or more intragenic mutations affecting two or more exons were also observed (Table I). Three changes deep within introns (non-coding) were also identified. Computerized morphometric analysis cleanly segregates all non-cancerous PTEN mutant tissues into a precancer, or EIN, group (FIG. 1) having a calculated D-Score<0. Morphometrically defined precancers are usually diagnosed by practicing pathologists as atypical endometrial hyperplasias.

TABLE 1

PTEN Mutation Endometrial Tissue Diagnosis

|  |  | PTEN Mutation[1] | |
| --- | --- | --- | --- |
| Endometrial Tissue | n | Total with Mutations | Mutation 2 exons |
| Cancer, Endometrioid | 30 | 83% (25) | 10% (3) |
| Precancer[2] (EIN) | 29 | 55% (16) | 3% (1) |
| Indeterminate[3] | — | — | — |
| Unopposed Estrogen Effect[4] | — | — | — |
| "Normal"[5] | 10 | 0% | 0% |
| Cancer, non-Endometrioid[6] | — | — | — |

[1]30 hysterectomies with endometrioid endometrial adenocarcinoma and co-existing regions of either premalignant or benign endometrial tissue were tested for all nine PTEN exon mutations. Although the distribution of multiple exonic hits between one or two alleles is unknown it provides some indication of that fraction of cases which are candidates for biallelic mutational inactivation.
[2]Precancers diagnosed by computerized morphometric analysis, D-Score <0. All cases independently confirmed by pathologist as EIN.
[3]Indeterminate by computerized morphometry, 0 < D < 1. Diagnosed by pathologist as EIN (6/9), unopposed estrogen (1/9), secretory endometrium (1/9), and unknown (1/9).
[4]Benign endometria by morphometry (D > 1), with stigmata of unopposed estrogen. Unstained glands were always admixed with staining glands.
[5]"Normal" tissues all were benign by morphometry, and included atrophic, inactive, or cycling endometrium. One severely atrophic endometrium contained no discernable PTEN protein.
[6]Non-endometrioid cancers included 2 undifferentiated carcinomas, 4 papillary serous carcinomas, and 2 malignant mixed Müllerian tumors.

Example 2

Introduction

PCR-based analysis to determine loss of heterozygosity of markers within or flanking PTEN was performed on the series of 30 endometrial carcinoma samples shown in Table 1.

Methods

For details on Tissue Samples, see Example 1, Methods.

Loss of Heterozygosity (LOH) Analysis

DNA from carcinoma and adjacent normal myometrium was amplified with PTEN linked primers D10S541, and D10S215 (MapPairs, Research Genetics Inc., Huntsville, Ala.) in the presence of $^{32}$P-TTP. PCR products of these polymorphic microsatellites were resolved on non-denaturing polyacrylamide gels(31;32), and resulting autoradiograms were visually assessed using a reference set of calibrated autoradiograms(26). Tumor allele intensities were compared to those of matched normal reference myometrium and scored as "LOH positive" when there was at least a 50% reduction of one allele.

Results

Overall, the loss of heterozygosity frequency was 23% (7/30) and all of these samples had PTEN mutations in the remaining allele indicating inactivation of both PTEN alleles. PCR testing for loss of heterozygosity of markers within or flanking PTEN showed an overall 10q23 LOH rate of 23% (7/30). One third (7/22) of cancers with intragenic mutations within a single PTEN exon had loss of the second allele by deletion.

Example 3

Introduction

The possibility of biallelic inactivation of PTEN and resultant lack of PTEN protein expression was assessed through the use of immunocytochemistry.

Methods

Tissue Samples

A second series of paraffin embedded endometrial tissues was assembled from the pathology files of Brigham and Women's Hospital, following approval by the Human Studies Committee at that institution. This series of endometrial tissues from 58 patients (38 hysterectomies, 20 curettings/biopsies) was used for PTEN immunohistochemistry. Cases were selected by report review for diagnoses of endometrial adenocarcinoma and/or anovulatory/hyperplastic endometrium.

Immunohistochemistry

Monoclonal antibody 6H2.1 raised against the last 100 C-terminal amino acids of PTEN (33) was used in all immunocytochemical analyses. Specificity has previously been demonstrated by Western blot of wild type and PTEN null cell lines, and successful blockade of paraffin section immunohistochemistry signal upon antibody pre-incubation with competing synthetic PTEN peptide (33).

Formalin fixed tissue samples were embedded in paraffin following standard histologic practices. Immunostaining was performed using a microwave antigen-retrieval protocol as described (33). Sections were incubated with monoclonal antibody 6H2.1 (dilution 1:100) for 1 hour at room temperature, washed, incubated with a secondary biotinylated horse anti-mouse IgG. Signal was detected by addition of avidin peroxidase and a chromogenic reaction carried out with 3-3' diaminobenzidine, which gives a brown reaction product. Intensity of epithelial staining was scored in methyl green counterstained slides from 0 (absent) to 3 (intense). PTEN immunohistochemistry using the 6H2.1 antibody requires freshly cut paraffin sections from recently embedded (within 6–12 months) tissues in order to maximize signal. Endometrial stroma and/or normal endometrial epithelium provided an internal positive control, and negative controls without addition of primary antibody showed low background in all cases.

Results

Table 1 and FIGS. 2 and 3 illustrate the salient PTEN immunohistochemical findings in malignant, premalignant, and estrogen driven endometria which were consistently seen in multiple independent patients with similar lesions. Endometrioid endometrial adenocarcinomas lost PTEN protein more frequently (61%) than non-endometrioid carcinomas (25%), although the small series does not show statistical significance (two-tailed Fishers exact test of tumor type by PTEN expression, p=0.115). Adjacent endometrial stroma was moderately PTEN positive, as were endothelial cells of blood vessels in immediate proximity to the tumor (FIG. 2, Panel A). Precancerous (EIN) lesions had no discernible PTEN protein in 75% of cases, most commonly in closely packed expanses of PTEN unstained glands offset by dispersed benign glands having a different cytology (FIG. 2, panels B–C). A less frequent pattern of heterogenous PTEN staining was seen in some "transitional" benign-precancer examples without cytologic changes (FIG. 3, Panels A–C). Two-tail Fishers exact test of cancer/EIN diagnosis by PTEN protein expression showed a non-significant (p=0.491) difference, although the small sample size limits the power of this comparison.

Whereas some unopposed estrogen-exposed endometria maintained ubiquitous epithelial PTEN expression, 28% had a background of PTEN staining glands punctuated by scattered negative glands. FIG. 3 shows endometria with heterogenous PTEN protein expression in which PTEN-negative glands may (FIG. 3, Panel E–F) or may not (FIG. 3, Panel B–C) display a cytology different than the surrounding PTEN expressing epithelia. Most areas of tubal change in disordered proliferative endometrium continue to express PTEN protein.

TABLE 2

PTEN Expression by Endometrial Tissue Diagnosis

| Endometrial Tissue | n | Absent | Mild | Moderate | Intense |
|---|---|---|---|---|---|
| Cancer, Endometrioid | 33 | 61% (20) | 12% (4) | 24% (8) | 3% (1) |
| Precancer[2] (EIN) | 12 | 75% (9) | 8% (1) | 17% (2) | 0% |
| Indeterminate[3] | 9 | 56% (5) | 11% (1) | 33% (3) | 0% |
| Unopposed Estrogen Effect[4] | 7 | 28.5% (2) | 0% | 28.5% (2) | 43% (3) |
| "Normal"[5] | 20 | 5% (1) | 45% (9) | 45% (9) | 5% (1) |

TABLE 2-continued

PTEN Expression by Endometrial Tissue Diagnosis

| Endometrial Tissue | n | Absent | Mild | Moderate | Intense |
|---|---|---|---|---|---|
| Cancer, non Endometrioid[6] | 8 | 25% (2) | 25% (2) | 25% (2) | 25% (2) |

[1]Antibody 6H2.1 immunohistochemistry, scored in epithelial cells.
[2]Precancers diagnosed by computerized morphometric analysis, D-Score < 0. All cases independently confirmed by pathologist as EIN.
[3]Indeterminate by computerized morphometry, 0 < D < 1. Diagnosed by pathologist as EIN (6/9), upopposed estrogen (1/9), secretory endometrium (1/9), and unknown (1/9).
[4]Benign endometria by morphometry (D > 1), with stigmata of unopposed estrogen. Unstained glands were always admixed with staining glands.
[5]"Normal" tissues all were benign by morphometry, and included atrophic, inactive, or cycling endometrium. One severly atrophic endometrium contained no discernable PTEN protein.
[6]Non-endometrioid cancers included 2 undifferentiated carcinomas, 4 papillary serous carcinomas, and 2 malignant mixed Müllerian tumors.

Example 4

Introduction

Case Selection 132 paraffin-embedded endometrial biopsies and curettings obtained in the years 1998–2000 (Department of Pathology, Brigham and Women's Hospital, Boston, Mass.) were allocated to proliferative, persistent proliferative, or EIN diagnostic classes based upon slide review consensus of two gynecologic pathologists. "Normal" proliferative endometria all came from premenopausal women less than 40 years of age (average age of 34.0±4.5) who were not taking supplemental hormones. Persistent proliferative endometria (mean age 45.2±9.3) had mitotically active but cytologically uniform glands with occasional cystically dilated glands, and were ascribed either to endogenous (anovulation) or exogenous (pharmacologic) estrogen sources based on clinical history. Endometrial polyps disqualified a case from the proliferative and persistent proliferative categories. EIN diagnosis (mean age 54.1±7.8) was made visually according to published criteria (41). The WHO endometrial hyperplasia classification system was not used in these studies because of its poor reproducibility, and discordance with discrete biologic groups defined by genetic analysis (40).

Ninety repeat biopsies were retrieved by diagnostic review from 45 individual women with proliferative endometrium on more than one occasion. Most repeat biopsies were symptomatically indicated (usually bleeding), but some were incidental to unrelated findings such as uterine fibroids, polyps.

Immunohistochemistry

Dewaxed rehydrated 4 μm paraffin sections underwent microwave antigen retrieval before adding primary anti-PTEN antibody 6H2.1 (Cascade Biosciences, Winchester, Mass., Cat.#ABM-2052) at 1:300 dilution. Anti-estrogen receptor antibody ER-ID5 (Dako), and anti-progesterone receptor antibody IA6 (Dako) were used at 1:300 and 1:100 dilutions, respectively. Primary antibody was incubated overnight at 4° C., washed, incubated with appropriate secondary biotinylated immunoglobulin (Vectastain ABC kit, Vector Laboratories, Inc., Burlingame, Calif.) and signal was detected by sequential addition of avidin peroxidase and 3,3'-diaminobenzidine. Epithelial staining was scored by two pathologists using endometrial stroma and/or normal endometrial epithelium as an internal positive control and negative run controls without addition of primary antibody. All tissue fragments were examined, and individual glands were scored as PTEN null when signal was absent in the nuclear and cytoplasmic compartments of most cells in that gland. Hormone receptors were scored by signal intensity in the nuclear compartment.

Genomic Analysis

Matched PTEN expressing and non-expressing proliferating endometrial epithelial cells were sampled using laser capture microdissection directed by PTEN immunohistochemistry of flanking serial sections. Approximately 10–50 ng of DNA per sample was PCR amplified using primers which define the coding region and flanking introns of all 9 PTEN gene exons. PCR products were subjected to denaturing gradient gel electrophoresis (DGGE), which was virtually 100% sensitive and specific in detecting sequence-confirmed PTEN mutations (37). DNA samples showing DGGE variants are re-subjected to PCR and semi-automated direct sequencing (ABI377a or PE3600 sequencers, Applied Biosystems, Foster City, Calif.).

For each patient, DNA from PTEN expressing and non-expressing epithelial cells was subjected to PTEN deletional analysis by PCR using 5*-tagged fluorophor primers, which amplify microsatellites flanking and within the PTEN gene, D10S579, D10S2491, and D10S541, and then electrophoresed through an ABI377a gel and analyzed with GeneScan software (42). Marker heterozygosity manifested as two peaks on a GeneScan gel, representing two different alleles present at that marker. Matched sets of DNA samples from PTEN expressing and non-expressing glands were compared at each marker and if one peak was reduced by at least a third, loss of heterozygosity (LOH) had occurred, which represented deletion of one of the alleles and usually, that chromosomal region.

Morphometry

A 1-mm circular window (surface area 0.785 mm) containing 100 randomly distributed points was superimposed on digitized photomicrographs of PTEN immunohistochemically stained endometria, and points over the fragment of interest (PTS100) tallied by composition of underlying tissue (stroma, STROMA 100; PTEN-expressing or "Positive" glands, POS100; PTEN-null glands, NULL100). Excluded were 7 fragmented or small (<½ sample window) samples, 4 cases diagnosed on hematoxylin and eosin slides as EIN in which the targeted PTEN-null glands did not involve the EIN focus, and one PTEN-null EIN focus which was distorted by tangential sectioning on recut. Surface area assigned to glands included combined epithelial and luminal compartments. Geometric centroids of each gland profile were marked, and the number of PTEN null (NULLCT) and expressing (POSCT) gland centroids within the window counted. Variables were calculated as follows: 1)VPS=100× (STROMA100/PTS100); 2)VPNULL=100×(NULL100/ PTS100); 3)VPPOS=100×(POS100/PTS100); 4)DENNULL=(NULLCT/PTS100)×(100 points in window/ 0.785 mm 2 window size); 5)DENPOS=(POSCT/PTS100)× (100 points in window/0.785 $mm^2$ window size); 6)SZNULL=(NULL100/NULLCT)(0.785 $mm^2$/100 points in window); 7)SZPOS=(POS100/NULLCT) (0.785 $mm^2$/ 100 points in window).

Results

Figure 4:
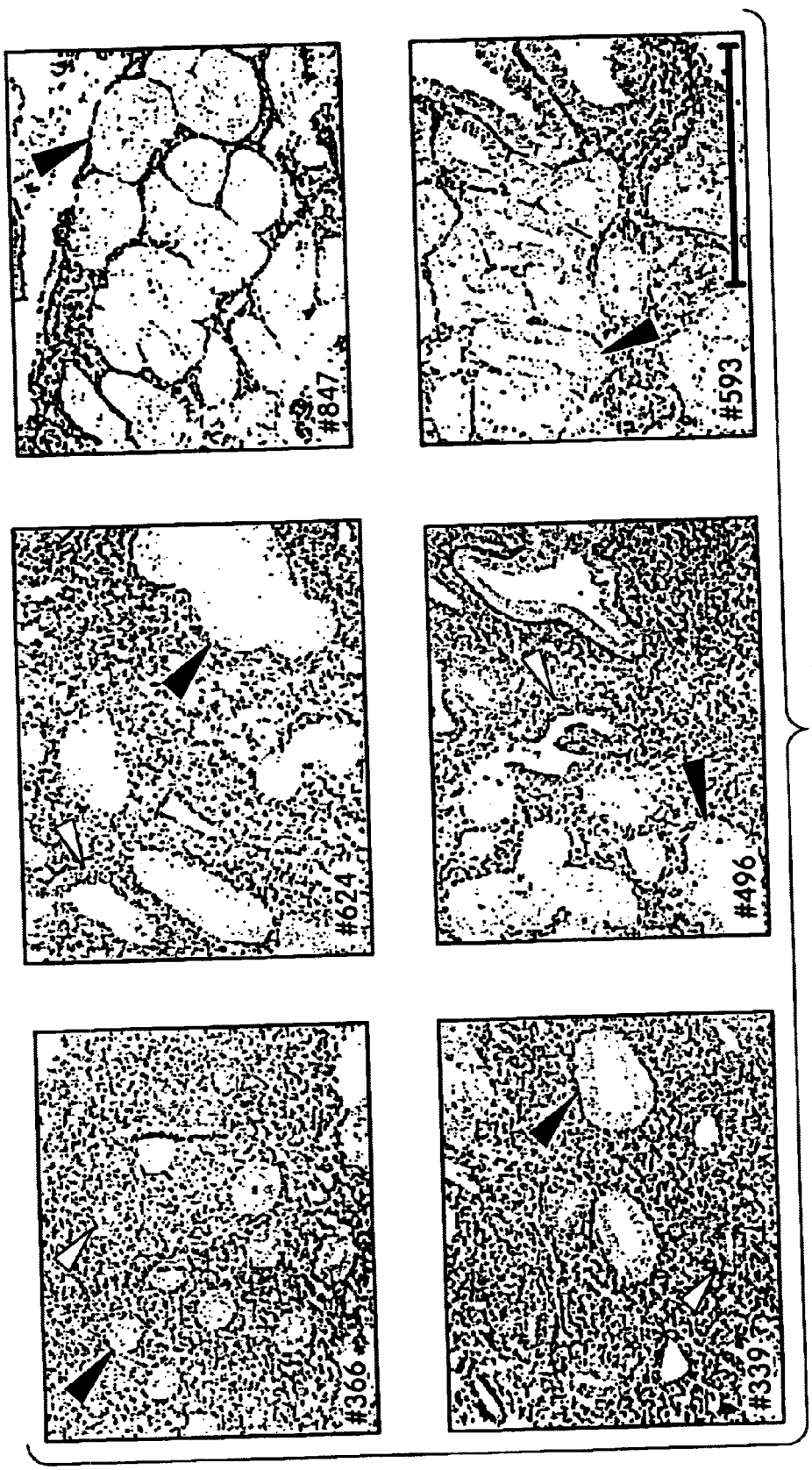
FIG. 4 is a digitized photomicrograph image of PTEN Immunohistochemistry in the endometrium. PTEN-null glands (examples indicated by black arrowhead) appear pale green against dark brown staining of surrounding stroma in proliferative (left, Cases 339, 366), persistent proliferative (center, Cases 624, 496), and EIN (right, Cases 847, 593) endometria from six different patients. Brown PTEN-positive glands (white arrowhead) are present in proliferative and persistent proliferative examples for comparison. Scale bar is 500 $\mu$m.

PTEN-null endometrial rates were 43, 56, and 63% in proliferative, persistent proliferative, and EIN diagnostic categories respectively (Table 3, FIG. 4). There was a linear trend by decade of age for increasing PTEN-null rates in older women (Coachman's test of linear trend, p=0.014). Average age of women with and without PTEN-null glands was 43.8 (±9.7) and 40.2 (±11.6) years, respectively. PTEN-null glands in the three diagnostic groups are present in women biopsied for a variety of reasons, so these results are applicable to a broad range of women seeking routine medical care (Table 3).

TABLE 3

Clinicopathologic features of endometria by PTEN immunohistochemistry, and slide diagnosis

| | | % PTEN-null by Diagnosis (fraction) | | | |
|---|---|---|---|---|---|
| | | Proliferative | Persistent Proliferative | EIN | Total |
| Sample | Curettage | 42.9 (6/14) | 54.5 (6/11) | 75.0 (6/8) | 54.5 (18/33) |
| | Biopsy | 42.9 (18/42) | 56.7(17/30) | 59.3 (16/27) | 51.5 (51/99) |
| Clinical Indication | Bleeding | 42.9 (12/28) | 56.3 (18/32) | 55.0 (11/20) | 51.3 (41/80) |
| | Infertility/ recurrent abortion | 41.7 (5/12) | 0.0 (0/0) | 100.0 (1/1) | 46.2 (6/13) |
| | Prior hyperplasia | 0.0 (0/1) | 0.0 (0/0) | 71.4 (5/7) | 75.0 (6/8) |
| | Anatomic (fibroids, septum, polyp, thick stripe) | 50.0 (3/6) | 100.0 (1/1) | 100.0 (1/1) | 62.5 (5/8) |

TABLE 3-continued

Clinicopathologic features of endometria by PTEN immunohistochemistry, and slide diagnosis

| | | % PTEN-null by Diagnosis (fraction) | | | |
|---|---|---|---|---|---|
| | | Proliferative | Persistent Proliferative | EIN | Total |
| | Other (pain, endometriosis) | 20 (1/5) | 33.3 (1/3) | 0.0 (0/2) | 20.0 (2/10) |
| | Unspecified | 75.0 (3/4) | 60.0 (3/5) | 100 (4/4) | 76.9 (10/13) |
| Hormones | Endogenous | 42.9 (24/56) | 55.9 (19/34) | 64.3 (18/28) | 51.7 (61/118) |
| | Exogenous | 0.0 (0/0) | 57.1 (4/7) | 57.1 (4/7) | 57.1 (8/14) |
| Meno- | Pre | 42.9 (24/56) | 57.1 (20/35) | 66.7 (14/21) | 51.8 (58/112) |
| pause | Post | 0.00 (0/0) | 50.0 (3/6) | 57.1 (8/14) | 55.0 (11/20) |
| Total | | 42.9 (24/56) | 56.1 (23/41) | 62.9 (22/35) | 52.3 (69/132) |

Figure 6A:
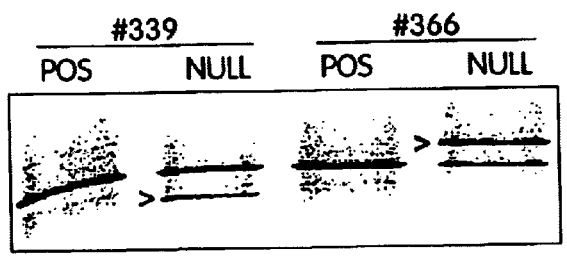
FIG. 6 is a digitized image (part a) of a single-plex PCR and denaturing gradient gel electrophoresis of the exon 5 of PTEN gene. DNA from PTEN-null glands (NULL) have aberrantly migrating species (arrowheads) compared to PTEN expressing (POS) glands. Bidirectional (for, forward; rev, reverse). The sequencing traces in part b illustrate direct sequence confirmation of mutations. PTEN immunohistochemistry of these two proliferative endometria (#366 and #399) is shown in FIG. 4, left-hand boxes.
Figure 6B:
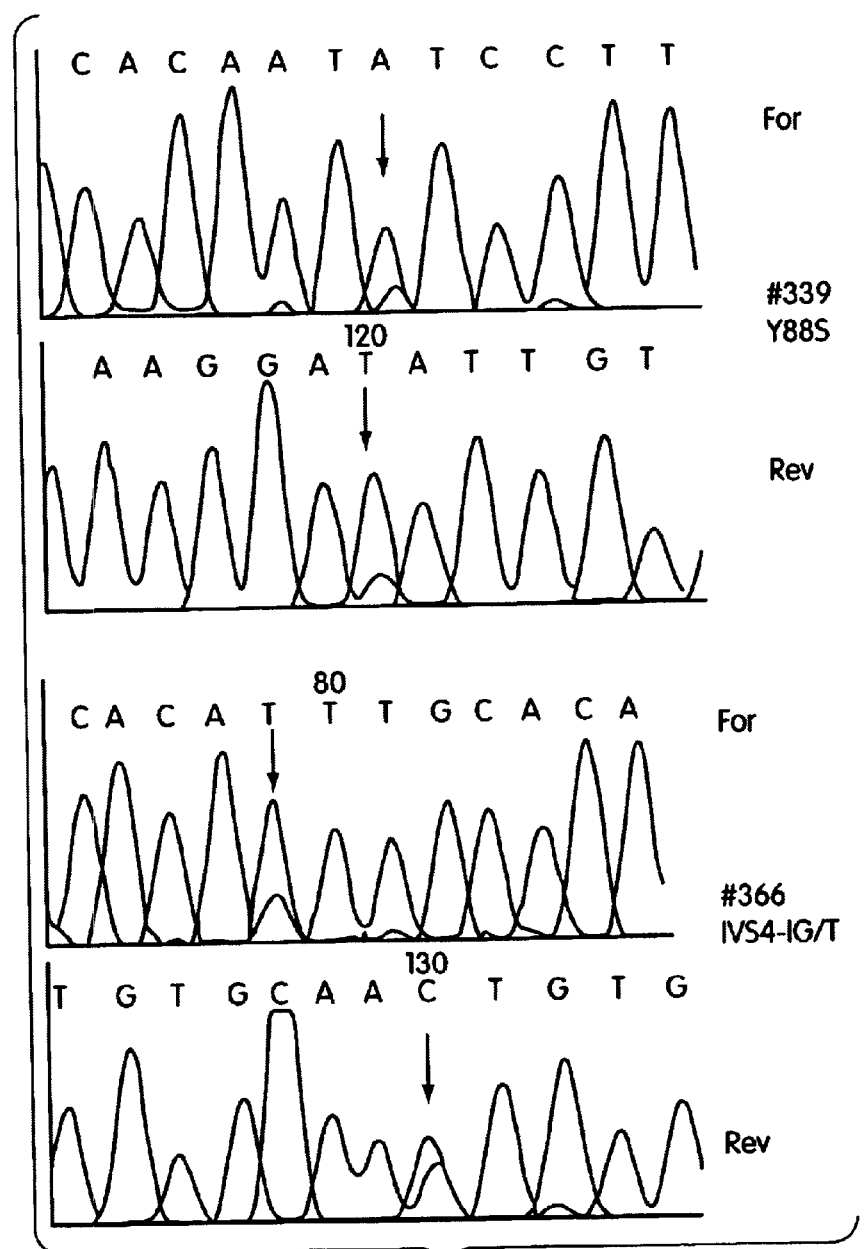

The occurrence of PTEN-null glands in 43% (24/56) of histologically normal proliferative endometrium (confirmed by staining two sections in each case) was unexpectedly high. In general, only a few histologically unaltered glands were PTEN-null among hundreds of proliferating glands in these otherwise unremarkable endometria. Since PTEN expression responds to the hormonal environment (43), estrogen and progesterone receptor immunohistochemistry were performed on flanking serial tissue sections and showed in all cases that the PTEN null and expressing glands in proliferative endometria retained comparable receptor quantities. Nineteen out of 24 proliferative endometria with PTEN-null glands had sufficient material for microdissection. Matched DNA from PTEN expressing and non-expressing glands from the same patient were co-processed for direct comparison of PTEN mutation and deletion (Tables 4 and 5). All PTEN-expressing matched control glands had a wild-type (normal) genotype whereas 84% (16/19) of non-expressing glands had a mutation (n=8) and/or loss of at least one 10q23 heterozygous marker (n=13) in the region of the PTEN locus. Results of denaturing gradient gel electrophoresis (DGGE), on products from single plex PCR on the exon 5 of the PTEN gene are shown in FIG. 6.

TABLE 4

PTEN Mutations in Proliferative Endometria: PTEN mutation, deletion and expression status.

| Patient # | Expression* | Mutation | LOH Status at Markers**: | | |
|---|---|---|---|---|---|
| | | | D10S579 | D10S2491 | D10S541 |
| 704 | + | None | NI | NI | ROH |
| 704 | − | None | NI | NI | LOH |
| 339 | + | None | ROH | ROH | NI |
| 339 | − | Y88S | LOH | ROH | NI |
| 521 | + | None | ROH | NI | ROH |
| 521 | − | None | LOH | NI | LOH |
| 366 | + | None | NI | NI | ROH |
| 366 | − | IVS4-1G > T | NI | NI | LOH |
| 932 | + | None | NI | ROH | NI |
| 932 | − | c963-8InsA | NI | ROH | NI |
| 603 | + | None | ROH | ROH | ROH |
| 603 | − | c462-473del12 | LOH | LOH | LOH |
| 471 | + | None | ROH | ROH | ROH |
| 471 | − | C643-5delT | LOH | ROH | ROH |
| 253 | + | None | ROH | NI | NI |

TABLE 4-continued

PTEN Mutations in Proliferative Endometria: PTEN mutation, deletion and expression status.

| Patient # | Expression* | Mutation | LOH Status at Markers**: | | |
|---|---|---|---|---|---|
| | | | D10S579 | D10S2491 | D10S541 |
| 253 | − | None | LOH | NI | NI |
| 479 | + | None | NI | ROH | ROH |
| 479 | − | None | NI | ROH | LOH |
| 071 | + | None | NI | ROH | NI |
| 071 | − | None | NI | ROH | NI |
| 075 | + | None | ROH | NI | NI |
| 075 | − | c462-473del12 | LOH | NI | NI |
| 908 | + | None | ROH | ROH | ROH |
| 908 | − | None | LOH | LOH | LOH |
| 106 | + | None | ROH | ROH | NI |
| 106 | − | None | LOH | LOH | NI |
| 613 | + | None | NI | ROH | ROH |
| 613 | − | None | NI | ROH | ROH |
| 039 | + | None | NI | ROH | ROH |
| 039 | − | None | NI | ROH | LOH |
| 229 | + | None | ROH | ROH | ROH |
| 229 | − | C988-90InsA | ROH | ROH | ROH |
| 421 | + | None | ROH | ROH | ROH |
| 421 | − | IVS4-1G > A | ROH | ROH | ROH |
| 717 | + | None | ROH | ROH | ROH |
| 717 | − | None | ROH | ROH | LOH |
| 469 | + | None | ROH | ROH | ROH |
| 469 | − | None | ROH | ROH | ROH |

*PTEN protein Null (−) and Positive (+) glands from individual biopsies.

**LOH, Loss of Heterozygosity (NI = not informative, ROH = retention of heterzygosity, LOH = loss of heterozygosity).

TABLE 5

Morphometric Characteristics of PTEN-null Glands, by Diagnosis within the Morphometry Window

| PTEN Parameter | Abbrev. | Units | Proliferative mean (SD) | Persistent Proliferative Mean (SD) | EIN mean (SD) | p* |
|---|---|---|---|---|---|---|
| Sample | n | Patients | 20 | 20 | 17 | |
| Volume % Stroma | VPS | percentage | 78.3 (10.2) | 65.2 (13.7) | 35.0 (7.9) | <0.001 |
| Volume% Null Gland | VPNULL | percentage | 13.0 (10.1) | 25.6 (17.7) | 63.9 (8.7) | <0.001 |
| Volume % Positive Glands | VPPOS | percentage | 8.7 (5.4) | 9.2 (1.1) | 1.1 (1.9) | 0.001 |
| Density of Null Glands | DENNULL | # glands/mm$^2$ | 8.4 (5.1) | 9.8 (6.6) | 26.2 (8.0) | <0.001 |
| Density of Positive Glands | DENPOS | # glands/mm$^2$ | 10.5 (8.7) | 3.5 (3.3) | 0.9 (1.7) | <0.001 |
| Size of Null Glands | SZNULL | mm$^2$ per gland | 0.016 (0.010) | 0.030 (0.017) | 0.026 (0.007) | <0.004 |
| Size of Positive Glands | SZPOS | mm$^2$ per gland | 0.014 (0.015) | 0.024 (0.012) | 0.018 (0.015) | <0.090 |

*two-tailed ANOVA, significance

The appearance of rare histologically normal glands harboring PTEN mutations would be inconsequential if they are completely shed with normal menstruation. Thus, PTEN immunohistochemistry was performed on 34 premenopausal women (no hormonal therapy, average age 42.3±6.2 years) with unremarkable proliferative endometrium on two separate occasions (interval averaged 400 days, range 26–1167 days). Twelve of 34 women had PTEN-null glands initially (Table 6), scattered throughout varying depths of the endometrial thickness, and 83% (10/12) of these continued to be present on follow-up. PTEN status of paired biopsies in Table 6 is highly associated with initial phenotype (Fishers exact test p=0.01, with an Odds Ratio of 10.71). A woman with PTEN-null glands in her endometrium is five times more likely to have PTEN-null glands on repeat biopsy than not. A separate series of 11 postmenopausal women (mean age 58.1±2.6 years) with two proliferative endometria separated by an average of 494 days (range 142–985 days) and sampled during the estrogenic phase of sequential estrogen/progestin replacement therapy were used for PTEN immunohistochemistry. Two had PTEN-null glands initially, retained by one on follow-up. 11% (1/9) with PTEN expressing first biopsies developed PTEN-null glands in the second biopsy. These 11 patients are not shown in Table 6, but when pooled with those of Table 6 increased the association of PTEN status between first and second biopsy (Fishers exact p<0.001, Odds Ratio 17.3).

TABLE 6

PTEN status in repeat biopsies of premenopausal women with endogenously cycling proliferative endometrium*.

| | 2$^{nd}$ Sample PTEN-positive | 2$^{nd}$ Sample PTEN-null | Total |
|---|---|---|---|
| 1$^{st}$ Sample PTEN-positive | 15 | 7 | 22 |
| 1$^{st}$ Sample PTEN-null | 2 | 10 | 12 |
| Total | 17 | 17 | 34 |

*Initial (1$^{st}$ sample) and repeat (2$^{nd}$ sample) endometrial samples scored as PTEN-nonexpressing (null) or having only PTEN-expressing glands (positive).

Figure 5:
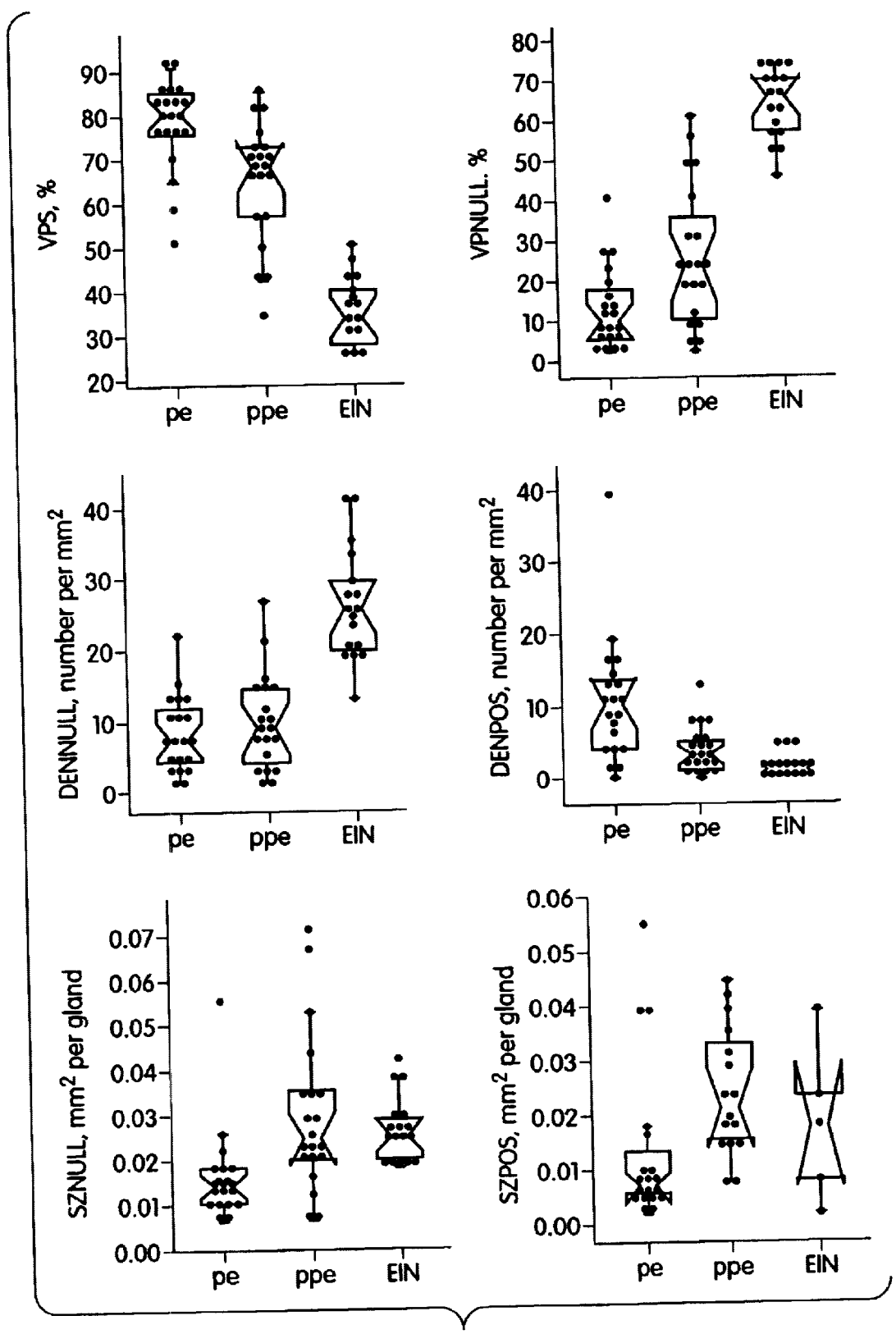
FIG. 5 is a diagram of a box-plot of PTEN-null gland morphometric variables (y axis), x axis arranged from left to right in order if a putative progression sequence of proliferative (PE, n=20), persistent proliferative (PPE, n=20) and EIN (n=17) endometria stained for PTEN protein. Volume percentage stroma (VPS) declines steadily because of increasing PTEN-null gland volume (VPNULL). Two elements sequentially contribute to rising VPNULL. The first, in the proliferative to persistent proliferative transition, is enlargement of individual PTEN-null glands (SZNULL). The density of PTEN-null glands (DENNULL) then increases between persistent proliferative and EIN endometria. PTEN expressing glands increase in size (SZPOS) in the proliferative to persistent proliferative transition but rapidly decline in density.

Changes in the histological structure of PTEN-null clones were documented by morphometric analysis of PTEN-immunostained normal proliferative, persistent proliferative, and EIN endometria (FIG. 5).

REFERENCES (1) Risinger J I, Hayes A K, Berchuck A, Barrett J C. PTEN/MMAC1 mutations in endometrial cancers. Cancer Res 1997; 57:4736–4738.

(2) Tashiro H, Blazes M S, Wu R, Cho K R, Bose S, Wang S I et al. Mutations in PTEN are frequent in endometrial carcinoma but rare in other common gynecological malignancies. Cancer Res 1997; 57:3935–3940.

(3) Peiffer S L, Herzog T J, Tribune D J, Mutch D G, Gersell D J, Goodfellow P J. Allelic loss of sequences from the long arm of chromosome 10 and replication errors in endometrial cancers. Cancer Res 1995; 55:1922–1926.

(4) Nagase S, Yamakawa H, Sato S, Yajima A, Horii A. Identification of a 790-kilobase region of common allelic loss in chromosome 10q25–q26 in human endometrial cancer. Cancer Res 1997; 57:1630–1633.

(5) Podsypanina K, Ellenson L H, Nemes A, Gu J, Tamura M, Yamada K M et al. Mutation of Pten/Mmac1 in mice causes neoplasia in multiple organ systems. Proc Natl Acad Sci U S A 1999; 96:1563–8.

(6) Liaw D, Marsh D J, Li J, Dahia P L, Wang S I, Zheng Z et al. Germline mutations of the PTEN gene in Cowden disease, an inherited breast and thyroid cancer syndrome. Nature Genet 1997; 16:64–67.

(7) Marsh D, Coulon V, Lunetta K, Rocca-Serra P, Dahia P, Zheng Z et al. Mutation spectrum and genotype-phenotype analyses in Cowden Disease and Bannayan-Zonana Syndrome, 2 hamartoma syndromes with germline PTEN mutation. Hum Mol Genet 1998; 7:507–515.

(8) Eng C. Genetics of Cowden syndrome: through the looking glass of oncology. Int J Oncol 1998; 12:701–710.

(9) Silverberg S, Sasano N, Yajima A. Endometrial carcinoma in Miyagi Prefecture, Japan: histopathologic analysis of a cancer-based series and comparison with cases in American women. Cancer (Phila) 1982; 49:1504–1510.

(10) Sherman M E, Sturgeon S, Brinton L, Kurman R J. Endometrial cancer chemoprevention: Implications of diverse pathways of carcinogenesis. J Cell Biochem 1995; 59 Suppl. 23:160–164.

(11) Parazzini F, La Vecchia C, Bocciolone L, Franceschi S. The epidemiology of endometrial cancer. Gynecol Oncol 1991; 41:1–16.

(12) Baak J P A, Nauta J, Wisse-Brekelmans E, Bezemer P. Architectural and nuclear morphometrical features together are more important prognosticators in endometrial hyperplasias than nuclear morphometrical features alone. J Pathol 1988; 154:335–341.

(13) Mutter G L, Wada H, Faquin W, Enomoto T. K-ras mutations appear in the premalignant phase of both microsatellite stable and unstable endometrial carcinogenesis. Mol Pathol 1999; 52:257–262.

(14) Jovanovic A S, Boynton K A, Mutter G L. Uteri of women with endometrial carcinoma contain a histopathologic spectrum of monoclonal putative precancers, some with microsatellite instability. Cancer Res 1996; 56:1917–1921.

(15) Mutter G L, Boynton K A, Faquin W C, Ruiz R E, Jovanovic A S. Allelotype mapping of unstable microsatellites establishes direct lineage continuity between endometrial precancers and cancer. Cancer Res 1996; 56:4483–4486.

(16) Scully R E, Bonfiglio T A, Kurman R J, Silverberg S G, Wilkinson E J. Uterine corpus. Histological Typing of Female Genital Tract Tumors. New York: Springer-Verlag, 1994: 13–31.

(17) Winkler B, Alvarez S, Richart R, Crum C. Pitfalls in the diagnosis of endometrial neoplasia. Obstet Gynecol 1984; 64:185–194.

(18) Kendall B S, Ronnett B M, Isacson C, Cho K R, Hedrick L, Diener-West M et al. Reproducibility of the diagnosis of endometrial hyperplasia, atypical hyperplasia, and well-differentiated carcinoma. Am J Surg Pathol 1998; 22:1012–1019.

(19) Maxwell G, Risinger J, Gumbs C, Shaw H, Bentley R, Barrett J et al. Mutation of the PTEN tumor supressor gene in endometrial hyperplasias. Cancer Res 1998; 58:2500–2503.

(20) Levine R L, Cargile C B, Blazes M S, Van Rees B, Kurman R J, Ellenson L H. PTEN mutations and microsatellite instability in complex atypical hyperplasia, a precursor lesion to uterine endometrioid carcinoma. Cancer Res 1998; 58:3254–3258.

(21) Yoshinaga K, Sasano H, Furukawa T, Yamakawa H, Yuki M, Sato S et al. The PTEN, BAX, and IGFIIR genes are mutated in endometrial atypical hyperplasia. Jpn J Cancer Res 1998; 89(10):985–990.

(22) Colgan T J, Norris H J, Foster W, Kurman R J, Fox C H. Predicting the outcome of endometrial hyperplasia by quantitative analysis of nuclear features using a linear discriminant function. Int J Gynecol Pathol 1983; 1:347–352.

(23) Dunton C, Baak J, Palazzo J, van Diest P, McHugh M, Widra E. Use of computerized morphometric analyses of endometrial hyperplasias in the prediction of coexistent cancer. Am J Obstet Gynecol 1996; 174:1518–1521.

(24) Mutter G L, Baak J P A, Crum C P, Richart R M, Ferenczy A, Faquin W C. Endometrial precancer diagnosis by histopathology, clonal analysis, and computerized morphometry. J Pathol 2000; (In Press).

(25) Baak J P A. Manual of Quantitative Pathology in Cancer Diagnosis and Prognosis. 1991. New York, Springer-Verlag.

(26) Mutter G L, Boynton K A. X chromosome inactivation in the normal female genital tract: Implications for identification of neoplasia. Cancer Res 1995; 55:5080–5084.

(27) Mutter G L, Chaponot M, Fletcher J. A PCR assay for non-random X chromosome inactivation identifies monoclonal endometrial cancers and precancers. Am J Pathol 1995; 146:501–508.

(28) Mutter G L, Boynton K A. PCR bias in amplification of androgen receptor alleles, a trinucleotide repeat marker used in clonality studies. Nucleic Acids Res 1995; 23:1411–1418.

(29) Dahia P, Fitzgerald M, Zhang X, Marsh D, Zheng Z, Pietsch T et al. A highly conserved processed PTEN pseudogene is located on chromosome band 9p21. Oncogene 1998; 16:2403–2406.

(30) Marsh D J, Dahia P L, Caron S, Kum J B, Frayling I M, Tomlinson I P et al. Germline PTEN mutations in Cowden syndrome-like families. J Med Genet 1998; 35:881–885.

(31) Pinto A P, Lin M C, Mutter G L, Sun D, Villa L L, Crum C P. Allelic loss in human papillomavirus-positive and -negative vulvar squamous cell carcinomas. Am J Pathol 1999; 154:1009–15.

(32) Lin M C, Mutter G L, Trivijisilp P, Boynton K A, Sun D, Crum C P. Patterns of allelic loss (LOH) in vulvar squamous carcinomas and adjacent noninvasive epithelia. Am J Pathol 1998; 152:1313–1318.

(33) Perren A, Weng L, Boag A, Ziebold U, Thakore K, Dahia P et al. Immunocytochemical evidence of loss of PTEN expression in primary ductal adenocarcinomas of the breast. Am J Pathol 1999; 155:1253–1260.

(34) Bergeron C, Nogales F, Masseroli M, Abeler V, Duvillard P, Muller-Holzner E et al. A multicentric European study testing the reproducibility of the WHO Classification of endometrial hyperplasia with a proposal of a simplified

(35) Gray L, Christopherson W, Hoover R. Estrogens and endometrial carcinoma. Obstet Gynecol 1977; 49:385–389.

(36) Weiss N, Sayvetz T. Incidence of endometrial cancer in relation to the use of oral contraceptives. N Engl J Med 1980; 302:551–554.

(37) Dahia P L M, Aguiar R C T, Alberta J, Kum J B, Caron S, Sill H et al. PTEN is inversely correlated with the cell survival factor Akt/PKB and is inactivated via multiple me chanismsin haematological malignancies. Hum Mol Genet 1999; 8:185–193.

(38) Eng C, Vijg J. Genetic testing: the problems and the promise. Nat Biotechnol 1997; 15:422–426.

(39) FitzGerald M G, Marsh D J, Wahrer D, Bell D, Caron S, Shannon K E et al. Germline mutations in PTEN are an infrequent cause of genetic predisposition to breast cancer. Oncogene 1998; 17:727–731.

(40) Mutter, G. L., Baak, J. P. A., Crum, C. P., Richart, R. M., Ferenczy, A., and Faquin, W. C. Endometrial precancer diagnosis by histopathology, clonal analysis, and computerized morphometry. J.Pathol., 190: 462–469, 2000.

(41) Mutter, G. L. Histopathology of genetically defined endometrial precancers. Int. J. Gynecological Pathology, 19: 301–309, 2000.

(42) Marsh, D., Dahia, P., Coulon, V., Zheng, Z., Dorion-Bonnett, F., Call, K., Little, R., Lin, A., Goldstein, A., Eeles, R., Hodgson, S., Richardson, A., Robinson, B., Weber, H., Longy, M., and Eng, C. Allelic imbalance, including deletion of PTEN/MMAC I at the Cowden disease locus on 10q22–23 in hamartomas from patients with Cowden disease and germline PTEN mutation. Genes Chrom. Cancer, 21: 61–69, 1998.

(43) Mutter, G. L., Lin, M. C., Fitzgerald, J. T., Kum, J. B., Ziebold, U., and Eng, C. Changes in endometrial PTEN expression throughout the human menstrual cycle. J. Clin. Endocrinol. Metab., 85: 2334–2338, 2000.

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

We claim:

1. A method for determining the likelihood of a group of endometrial cells or an endometrial gland to become cancerous, comprising
performing immunohistochemistry on a group of endometrial cells or one or more endometrial glands using PTEN antibody or an antigen-binding fragment thereof and
determining the binding of the PTEN antibody or antigen-binding fragment thereof to the group of endometrial cells or glands, wherein a reduced amount of PTEN antibody or antigen-binding fragment thereof bound to the group of endometrial cells or glands relative to a control group of cells indicates that the group of endometrial cells or glands has an increased likelihood of becoming cancerous.

2. The method of claim 1, wherein the antibody or antigen-binding fragment thereof is 6H2.1 antibody or an antigen-binding fragment thereof.

3. The method of claim 1, wherein the group of endometrial cells or the one or more endometrial glands and the control group of cells are present in a tissue sample.

4. The method of claim 1, wherein the control group of cells and the group of endometrial cells or glands are the same cell type and wherein the amount of binding of the PTEN antibody or antigen-binding fragment thereof to the group of endometrial cells or glands is 50% or less of the binding of the PTEN antibody or antigen-binding fragment thereof to the control group of cells.

5. The method of claim 1, further comprising determining the size of a group of endometrial cells or one or more endometrial glands which have reduced PTEN expression, wherein an increased size of the group of endometrial cells or the glands relative to a control group of cells or glands indicates that the group of endometrial cells or glands has an increased likelihood of becoming cancerous.

6. The method of claim 1, wherein the subject is receiving or has received unopposed estrogen treatment.

7. A method for monitoring the progression of endometrial precancers, comprising,
determining the expression of PTEN in endometrial cells or glands by immunohistochemistry of an endometrial tissue sample obtained at a first time using a PTEN antibody or an antigen-binding fragment thereof,
determining the expression of PTEN in endometrial cells or glands by immunohistochemistry of an endometrial tissue sample obtained at a second time using the PTEN antibody or antigen-binding fragment thereof,
comparing the expression of PTEN in the endometrial cells or glands at the first time and the second time, wherein reduced expression of PTEN at the second time relative to the first time indicates progression of endometrial precancers to a cancerous stage.

8. The method of claim 7, wherein the antibody or antigen-binding fragment thereof is 6H2.1 antibody or antigen-binding fragment thereof.

9. The method of claim 7, further comprising
determining the size of groups of endometrial cells or glands which have reduced PTEN expression in the endometrial tissue sample obtained at the first time and the endometrial tissue sample obtained at the second time, and
comparing the size of the groups of endometrial cells or the glands which have reduced PTEN expression at the first time and the second time, wherein increased size of the groups of endometrial cells or the glands which have reduced PTEN expression at the second time relative to the first time indicates progression of endometrial precancers to a cancerous stage.

10. The method of claim 9, wherein the subject is receiving or has received unopposed estrogen treatment.

11. The method of claim 7, wherein the subject is undergoing drug therapy for endometrial precancer or endometrial cancer.

12. A method for diagnosing endometrial precancer in a subject comprising
obtaining a biological sample of endometrial tissue or cells from a subject,
contacting the sample with an endometrial cell marker that specifically binds to endometrial cells,
contacting the sample with an antibody or antigen-binding fragment thereof that specifically binds PTEN,
determining specific binding between the antibody or antigen-binding fragment thereof and PTEN in the sample, and
determining the specific binding between the endometrial cell marker, and agents in the sample.

13. The method of claim 12, further comprising
comparing the determination of specific binding of the antibody or antigen-binding fragment thereof and the specific binding of the endometrial cell marker in the sample, to the specific binding of the antibody or antigen-binding fragment thereof and the specific binding of the endometrial cell marker in a control group of cells as a diagnosis for endometrial precancer in the subject.

14. The method of claim 12, wherein the antibody or antigen-binding fragment thereof is 6H2.1 antibody or an antigen-binding fragment thereof.

15. The method of claim 12, wherein the endometrial cell marker is selected from the group consisting of: antibodies and antigen-binding fragments thereof, and ligands.

16. The method of claim 12, wherein the endometrial cell marker comprises an anti-estrogen receptor antibody or an anti-progesterone receptor antibody.

17. The method of claim 12, wherein the endometrial cell marker comprises estrogen or progesterone.

18. A method for evaluating the effect of candidate pharmacological compounds on endometrial precancer cell phenotype comprising culturing endometrial tissue or cells, contacting the cultured endometrial tissue or cells with an antibody or antigen fragment thereof that specifically binds to PTEN, determining a first amount of specific binding of the antibody or antigen fragment thereof with the endometrial tissue or cells, contacting the cultured endometrial tissue or cells with a candidate pharmacological agent, contacting the cultured endometrial tissue or cells with the antibody or antigen-binding fragment thereof, determining a second amount of specific binding of the antibody or antigen-binding fragment thereof, with the cultured endometrial tissue or cells, and comparing the first and second amounts of specific binding of the antibody or antigen-binding fragment thereof to the tissue or cells, wherein a change in the second amount of specific binding of the antibody or antigen-binding fragment thereof, relative to the first amount of specific binding of the antibody or antigen-binding fragment thereof, indicates the candidate pharmacological compound alters the level of PTEN, wherein a decrease in the relative amount of PTEN indicates the onset of or progression of an endometrial precancer cell phenotype, and where an increase in the relative amount of PTEN indicates the regression of an endometrial precancer cell phenotype.

19. The method of claim 18, wherein the antibody or antigen-binding fragment thereof is 6H2.1 antibody or an antigen-binding fragment thereof.

20. The method of claim 18, wherein the endometrial tissue or cells are not suspected of having endometrial cancer.

* * * * *

SEQUENCE LISTING

```
<160> NUMBER OF SEQ ID NOS: 20

<210> SEQ ID NO 1
<211> LENGTH: 22
<212> TYPE: DNA
<213> ORGANISM: Homo sapiens

<400> SEQUENCE: 1
cgtctgccat ctctctcctc ct                                        22

<210> SEQ ID NO 2
<211> LENGTH: 70
<212> TYPE: DNA
<213> ORGANISM: Homo sapiens

<400> SEQUENCE: 2
cgcccgccgc gccccgcgcc cggcccgccg ccccgcccg aaataataaa tccgtctact  60
cccacgttct                                                      70

<210> SEQ ID NO 3
<211> LENGTH: 30
<212> TYPE: DNA
<213> ORGANISM: Homo sapiens

<400> SEQUENCE: 3
cgtcccgcgt ttgattgctg catatttcag                                30

<210> SEQ ID NO 4
<211> LENGTH: 61
<212> TYPE: DNA
<213> ORGANISM: Homo sapiens

<400> SEQUENCE: 4
cgcccgccgc gccccgcgcc cgtcccgccg ccccgcccg tctaaatgaa aacacaacat  60
``` g                                                                61

<210> SEQ ID NO 5
<211> LENGTH: 60
<212> TYPE: DNA
<213> ORGANISM: Homo sapiens

<400> SEQUENCE: 5
cgcccgccgc gccccgcgcc cggcccgccg ccccgcccg taaatggtat ttgagattag    60

<210> SEQ ID NO 6
<211> LENGTH: 25
<212> TYPE: DNA
<213> ORGANISM: Homo sapiens

<400> SEQUENCE: 6
gcgcgaagat atttgcaagc ataca                                        25

<210> SEQ ID NO 7
<211> LENGTH: 72
<212> TYPE: DNA
<213> ORGANISM: Homo sapiens

<400> SEQUENCE: 7
cgcccgccgc gccccgcgcc cgtcccgccg ccccgcccg aaataataaa cattataaag    60
attcaggcaa tg                                                      72

<210> SEQ ID NO 8
<211> LENGTH: 21
<212> TYPE: DNA
<213> ORGANISM: Homo sapiens

<400> SEQUENCE: 8
gacagtaaga tacagtctat c                                            21

<210> SEQ ID NO 9
<211> LENGTH: 63
<212> TYPE: DNA
<213> ORGANISM: Homo sapiens

<400> SEQUENCE: 9
cgcccgccgc gccccgcgcc cgtcccgccg ccccgcccg ttttttctta ttctgaggtt    60
atc                                                                63

<210> SEQ ID NO 10
<211> LENGTH: 19
<212> TYPE: DNA
<213> ORGANISM: Homo sapiens

<400> SEQUENCE: 10
tcattacacc agttcgtcc                                               19

<210> SEQ ID NO 11
<211> LENGTH: 19
<212> TYPE: DNA
<213> ORGANISM: Homo sapiens

<400> SEQUENCE: 11
tcatgttgca gcaattcac                                               19

<210> SEQ ID NO 12
<211> LENGTH: 61

-continued

```
<212> TYPE: DNA
<213> ORGANISM: Homo sapiens

<400> SEQUENCE: 12
cgcccgccgc gccccgcgcc cgtcccgccg ccccccgcccg gaagaggaaa ggaaaaacat    60
c                                                                     61

<210> SEQ ID NO 13
<211> LENGTH: 25
<212> TYPE: DNA
<213> ORGANISM: Homo sapiens

<400> SEQUENCE: 13
gcgcgtttca atttggcttc tcttt                                           25

<210> SEQ ID NO 14
<211> LENGTH: 70
<212> TYPE: DNA
<213> ORGANISM: Homo sapiens

<400> SEQUENCE: 14
cgcccgccgc gccccgcgcc cggcccgccg ccccccgcccg aaataataaa taagaaaact    60
gttccaatac                                                            70

<210> SEQ ID NO 15
<211> LENGTH: 28
<212> TYPE: DNA
<213> ORGANISM: Homo sapiens

<400> SEQUENCE: 15
cgtcccgcaa tactggtatg tatttaac                                        28

<210> SEQ ID NO 16
<211> LENGTH: 60
<212> TYPE: DNA
<213> ORGANISM: Homo sapiens

<400> SEQUENCE: 16
cgcccgccgc gccccgcgcc cggcccgccg ccccccgcccg gatatttctc ccaatgaaag    60

<210> SEQ ID NO 17
<211> LENGTH: 22
<212> TYPE: DNA
<213> ORGANISM: Homo sapiens

<400> SEQUENCE: 17
cggtttcact tttgggtaaa ta                                              22

<210> SEQ ID NO 18
<211> LENGTH: 60
<212> TYPE: DNA
<213> ORGANISM: Homo sapiens

<400> SEQUENCE: 18
cgcccgccgc gccccgcgcc cgtcccgccg ccccccgcccg accccacaa aatgtttaat    60

<210> SEQ ID NO 19
<211> LENGTH: 60
<212> TYPE: DNA
<213> ORGANISM: Homo sapiens

<400> SEQUENCE: 19
```

-continued

```
cgcccgccgc gccccgcgcc cggcccgccg ccccgcccg tcactaaata gtttaagatg        60
```

<210> SEQ ID NO 20
<211> LENGTH: 20
<212> TYPE: DNA
<213> ORGANISM: Homo sapiens

<400> SEQUENCE: 20

```
ttcattctct ggatcagagt                                                   20
```